United States Patent
Shelton, IV et al.

(10) Patent No.: US 11,779,332 B2
(45) Date of Patent: Oct. 10, 2023

(54) POWERED SURGICAL STAPLER HAVING INDEPENDENTLY OPERABLE CLOSURE AND FIRING SYSTEMS

(71) Applicant: Cilag GmbH International, Zug (CH)

(72) Inventors: Frederick E. Shelton, IV, Hillsboro, OH (US); Kevin M. Fiebig, Cincinnati, OH (US); Shane R. Adams, Lebanon, OH (US); Adam D. Hensel, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 53 days.

(21) Appl. No.: 17/402,679

(22) Filed: Aug. 16, 2021

(65) Prior Publication Data
US 2023/0051756 A1  Feb. 16, 2023

(51) Int. Cl.
*A61B 17/072* (2006.01)
*A61B 17/00* (2006.01)

(52) U.S. Cl.
CPC .. *A61B 17/072* (2013.01); *A61B 2017/00022* (2013.01); *A61B 2017/00398* (2013.01);
(Continued)

(58) Field of Classification Search
CPC ........ A61B 17/072; A61B 2017/00022; A61B 2017/00398; A61B 2017/07271; A61B 2017/07278; A61B 2017/07285
(Continued)

(56) References Cited

U.S. PATENT DOCUMENTS

| 5,129,570 A | 7/1992 | Schulze et al. |
| 7,404,508 B2 | 7/2008 | Smith et al. |

(Continued)

FOREIGN PATENT DOCUMENTS

| WO | WO 2015/153642 A1 | 10/2015 |
| WO | WO 2017/083125 A1 | 5/2017 |

(Continued)

OTHER PUBLICATIONS

U.S. Appl. No. 17/402,674.
(Continued)

*Primary Examiner* — Dariush Seif
(74) *Attorney, Agent, or Firm* — Frost Brown Todd LLP

(57) ABSTRACT

An apparatus includes an end effector and a drive system. The drive system is configured to drive a jaw closure assembly to provide the end effector in a first closed position. The drive system is further configured to operatively disengage the jaw closure assembly and operatively engage a firing assembly, then distally advance a firing member to actuate the end effector. The drive system is further configured to detect an initiation condition; and in response to detecting the initiation condition, operatively disengage the firing assembly and operatively re-engage the jaw closure assembly. The drive system is further configured to drive the jaw closure assembly to provide the end effector in a second closed position, then operatively disengage the jaw closure assembly and operatively re-engage the firing assembly. The drive system is further configured to distally advance the firing member further within the end effector to further actuate the end effector.

15 Claims, 24 Drawing Sheets

(52) U.S. Cl.
CPC ............... *A61B 2017/07271* (2013.01); *A61B 2017/07278* (2013.01); *A61B 2017/07285* (2013.01)

(58) Field of Classification Search
USPC .......................................... 227/175.1–182.1
See application file for complete search history.

(56) References Cited

U.S. PATENT DOCUMENTS

| | | | |
|---|---|---|---|
| 7,434,715 | B2 | 10/2008 | Shelton, IV et al. |
| 7,568,603 | B2* | 8/2009 | Shelton, IV ..... A61B 17/07207 227/19 |
| 7,721,930 | B2 | 5/2010 | McKenna et al. |
| 7,810,692 | B2 | 10/2010 | Hall et al. |
| 7,832,408 | B2 | 11/2010 | Shelton, IV et al. |
| 7,845,537 | B2 | 12/2010 | Shelton, IV et al. |
| 8,083,120 | B2 | 12/2011 | Shelton, IV et al. |
| 8,210,411 | B2 | 7/2012 | Yates et al. |
| 8,408,439 | B2 | 4/2013 | Huang et al. |
| 8,453,914 | B2 | 6/2013 | Laurent et al. |
| 8,708,213 | B2 | 4/2014 | Shelton, IV et al. |
| 9,060,770 | B2 | 6/2015 | Shelton, IV et al. |
| 9,186,142 | B2 | 11/2015 | Fanelli et al. |
| 9,517,065 | B2 | 12/2016 | Simms et al. |
| 9,622,746 | B2 | 4/2017 | Simms et al. |
| 9,717,497 | B2 | 8/2017 | Zerkle et al. |
| 9,795,379 | B2 | 10/2017 | Leimbach et al. |
| 9,808,248 | B2 | 11/2017 | Hoffman |
| 9,839,487 | B2 | 12/2017 | Dachs, II |
| 10,011,018 | B2 | 7/2018 | McGrogan et al. |
| 10,092,292 | B2 | 10/2018 | Boudreaux et al. |
| 10,307,170 | B2 | 6/2019 | Parfett et al. |
| 10,485,621 | B2 | 11/2019 | Morrissette et al. |
| 10,500,007 | B2* | 12/2019 | Richmond ............. A61B 34/30 |
| 10,537,400 | B2 | 1/2020 | Dachs, II et al. |
| 10,610,313 | B2 | 4/2020 | Bailey et al. |
| 10,667,809 | B2 | 6/2020 | Bakos et al. |
| 10,806,530 | B2 | 10/2020 | Liao et al. |
| 10,863,988 | B2 | 12/2020 | Patel et al. |
| 11,020,138 | B2 | 6/2021 | Ragosta |
| 11,026,755 | B2 | 6/2021 | Weir et al. |
| 11,076,926 | B2 | 8/2021 | Ragosta et al. |
| 11,147,552 | B2 | 10/2021 | Burbank et al. |
| 11,166,773 | B2 | 11/2021 | Ragosta et al. |
| 11,234,700 | B2 | 2/2022 | Ragosta et al. |
| 11,259,884 | B2 | 3/2022 | Burbank |
| 2006/0185682 | A1 | 8/2006 | Marczyk |
| 2008/0300580 | A1* | 12/2008 | Shelton, IV ..... A61B 17/07207 606/1 |
| 2011/0295269 | A1* | 12/2011 | Swensgard ............ A61B 34/76 606/130 |
| 2012/0209314 | A1 | 8/2012 | Weir et al. |
| 2014/0239036 | A1* | 8/2014 | Zerkle ............. A61B 17/07207 227/175.1 |
| 2014/0263539 | A1* | 9/2014 | Leimbach .............. G16H 20/40 227/175.1 |
| 2014/0277017 | A1* | 9/2014 | Leimbach .......... A61B 18/1445 227/175.3 |
| 2015/0297228 | A1 | 10/2015 | Huitema et al. |
| 2016/0175036 | A1* | 6/2016 | Horner .................. H10N 30/03 29/25.35 |
| 2016/0361126 | A1 | 12/2016 | Schena et al. |
| 2017/0020617 | A1 | 1/2017 | Weir et al. |
| 2017/0215943 | A1* | 8/2017 | Allen, IV ........... A61B 18/1445 |
| 2017/0265865 | A1 | 9/2017 | Burbank |
| 2017/0265954 | A1 | 9/2017 | Burbank et al. |
| 2017/0296177 | A1* | 10/2017 | Harris .................... G16H 40/63 |
| 2017/0333037 | A1 | 11/2017 | Wellman et al. |
| 2018/0168756 | A1 | 6/2018 | Liao et al. |
| 2018/0271608 | A1 | 9/2018 | Ragosta et al. |
| 2018/0310935 | A1 | 11/2018 | Wixey |
| 2018/0325606 | A1 | 11/2018 | Weir et al. |
| 2018/0344419 | A1 | 12/2018 | Dachs, II et al. |
| 2019/0000446 | A1* | 1/2019 | Shelton, IV ........... A61B 34/30 |
| 2019/0000565 | A1* | 1/2019 | Shelton, IV ........... A61B 34/30 |
| 2019/0038371 | A1 | 2/2019 | Wixey et al. |
| 2019/0076142 | A1 | 3/2019 | Wixey |
| 2019/0076143 | A1 | 3/2019 | Smith |
| 2019/0099177 | A1* | 4/2019 | Yates ..................... A61B 90/98 |
| 2019/0167266 | A1 | 6/2019 | Patel et al. |
| 2019/0200989 | A1 | 7/2019 | Burbank et al. |
| 2019/0239967 | A1 | 8/2019 | Ragosta et al. |
| 2019/0262088 | A1 | 8/2019 | Burbank |
| 2019/0298355 | A1* | 10/2019 | Shelton, IV ..... A61B 17/07207 |
| 2019/0314015 | A1* | 10/2019 | Shelton, IV ..... A61B 17/07207 |
| 2020/0054320 | A1* | 2/2020 | Harris .................. A61B 17/064 |
| 2020/0138529 | A1 | 5/2020 | Ragosta et al. |
| 2020/0155151 | A1* | 5/2020 | Overmyer ............... A61B 34/71 |
| 2020/0397430 | A1 | 12/2020 | Patel et al. |
| 2020/0405301 | A1 | 12/2020 | Shelton, IV et al. |
| 2021/0186497 | A1* | 6/2021 | Shelton, IV ..... A61B 17/07207 |
| 2021/0393340 | A1 | 12/2021 | Beckman et al. |
| 2021/0401433 | A1 | 12/2021 | Freidel et al. |
| 2023/0051756 | A1* | 2/2023 | Shelton, IV ......... A61B 17/072 |

FOREIGN PATENT DOCUMENTS

| | | | |
|---|---|---|---|
| WO | WO 2017/083129 | A1 | 5/2017 |
| WO | WO 2018/049198 | A1 | 3/2018 |
| WO | WO 2018/049206 | A1 | 3/2018 |
| WO | WO 2018/049211 | A1 | 3/2018 |
| WO | WO 2018/049217 | A1 | 3/2018 |
| WO | WO 2018/052806 | A1 | 3/2018 |
| WO | WO 2018/052810 | A1 | 3/2018 |
| WO | WO 2018/071497 | A1 | 4/2018 |
| WO | WO 2018/071763 | A1 | 4/2018 |
| WO | WO 2018/085529 | A2 | 5/2018 |
| WO | WO 2018/175467 | A1 | 9/2018 |
| WO | WO 2019/165403 | A1 | 8/2019 |
| WO | WO 2020/131290 | A1 | 6/2020 |

OTHER PUBLICATIONS

U.S. Appl. No. 17/402,675.
U.S. Appl. No. 17/402,677.
U.S. Appl. No. 17/402,695.
U.S. Appl. No. 17/402,701.
U.S. Appl. No. 17/402,703.
U.S. Appl. No. 17/402,720.
U.S. Appl. No. 17/402,732.
U.S. Appl. No. 17/402,738.
U.S. Appl. No. 17/402,744.
U.S. Appl. No. 17/402,749.
U.S. Appl. No. 17/402,759.
U.S. Appl. No. 17/088,941, entitled "Surgical Stapler End Effector Sled Having Cartridge Wall Support Feature," filed Nov. 4, 2020.
U.S. Appl. No. 17/402,674, entitled "Methods of Operating a Robotic Surgical Stapler," filed Aug. 16, 2021.
U.S. Appl. No. 17/402,675, entitled "Multi-Threshold Motor Control Algorithm for Powered Surgical Stapler," filed Aug. 16, 2021.
U.S. Appl. No. 17/402,677, entitled "Variable Response Motor Control Algorithm for Powered Surgical Stapler," filed Aug. 16, 2021.
U.S. Appl. No. 17/402,695, entitled "Firing System Features for Surgical Stapler," filed Aug. 16, 2021.
U.S. Appl. No. 17/402,701, entitled "Multiple-Sensor Firing Lockout Mechanism for Powered Surgical Stapler," filed Aug. 16, 2021.
U.S. Appl. No. 17/402,703, entitled "Proximally Located Firing Lockout Mechanism for Surgical Stapler," filed Aug. 16, 2021.
U.S. Appl. No. 17/402,720, entitled "Cartridge-Based Firing Lockout Mechanism for Surgical Stapler," filed Aug. 16, 2021.
U.S. Appl. No. 17/402,732, entitled "Multi-Position Restraining Member for Sled Movement," filed Aug. 16, 2021.
U.S. Appl. No. 17/402,738, entitled "Firing Member Tracking Feature for Surgical Stapler," filed Aug. 16, 2021.
U.S. Appl. No. 17/402,744, entitled "Adjustable Power Transmission Mechanism for Powered Surgical Stapler," filed Aug. 16, 2021.
U.S. Appl. No. 17/402,749, entitled "Firing Bailout System for Powered Surgical Stapler," filed Aug. 16, 2021.

(56) References Cited

OTHER PUBLICATIONS

U.S. Appl. No. 17/402,759, entitled "Deflectable Firing Member for Surgical Stapler," filed Aug. 16, 2021.

* cited by examiner

| TIME | OPERATION/FUNCTION | IMAGE |
|---|---|---|
| $t_0$ | NO TISSUE CONTACT | |
| $t_1$ | TISSUE CONTACT/ JAW CLOSURE | |
| $t_2$ | JAW CLOSED/ TISSUE COMPRESSION/ START FIRING I-BEAM | |
| $t_3$ | STOP FIRING I-BEAM/ ENGAGE JAW MOTOR TO INCREASE CLAMP FORCE | |
| $t_4$ | ENGAGE FIRING I-BEAM | |
| $t_5$ | STOP FIRING I-BEAM/ ENGAGE JAW MOTOR TO INCREASE CLAMP FORCE | |
| $t_6$ | ENGAGE FIRING I-BEAM | |
| $t_7$ | STOP FIRING I-BEAM/ MAX TRAVEL DISTANCE COMPOETED | |

FIG. 26

POWERED SURGICAL STAPLER HAVING INDEPENDENTLY OPERABLE CLOSURE AND FIRING SYSTEMS

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically surgical systems. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probe, etc. Each of these structures performs functions for the surgeon, for example, cutting tissue, coagulating tissue, holding or driving a needle, grasping a blood vessel, dissecting tissue, or cauterizing tissue.

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers and associated features are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued on Nov. 17, 2015; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 10,092,292, entitled "Staple Forming Features for Surgical Stapling Instrument," issued Oct. 9, 2018; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; and U.S. Pat. No. 8,210,411, entitled "Motor-Driven Surgical Instrument," issued Jul. 3, 2012. The disclosure of each of the above-cited U.S. Patents is incorporated by reference herein in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 26 depicts a table showing an exemplary use of the motor control algorithm of FIG. 25.

Figure 1:
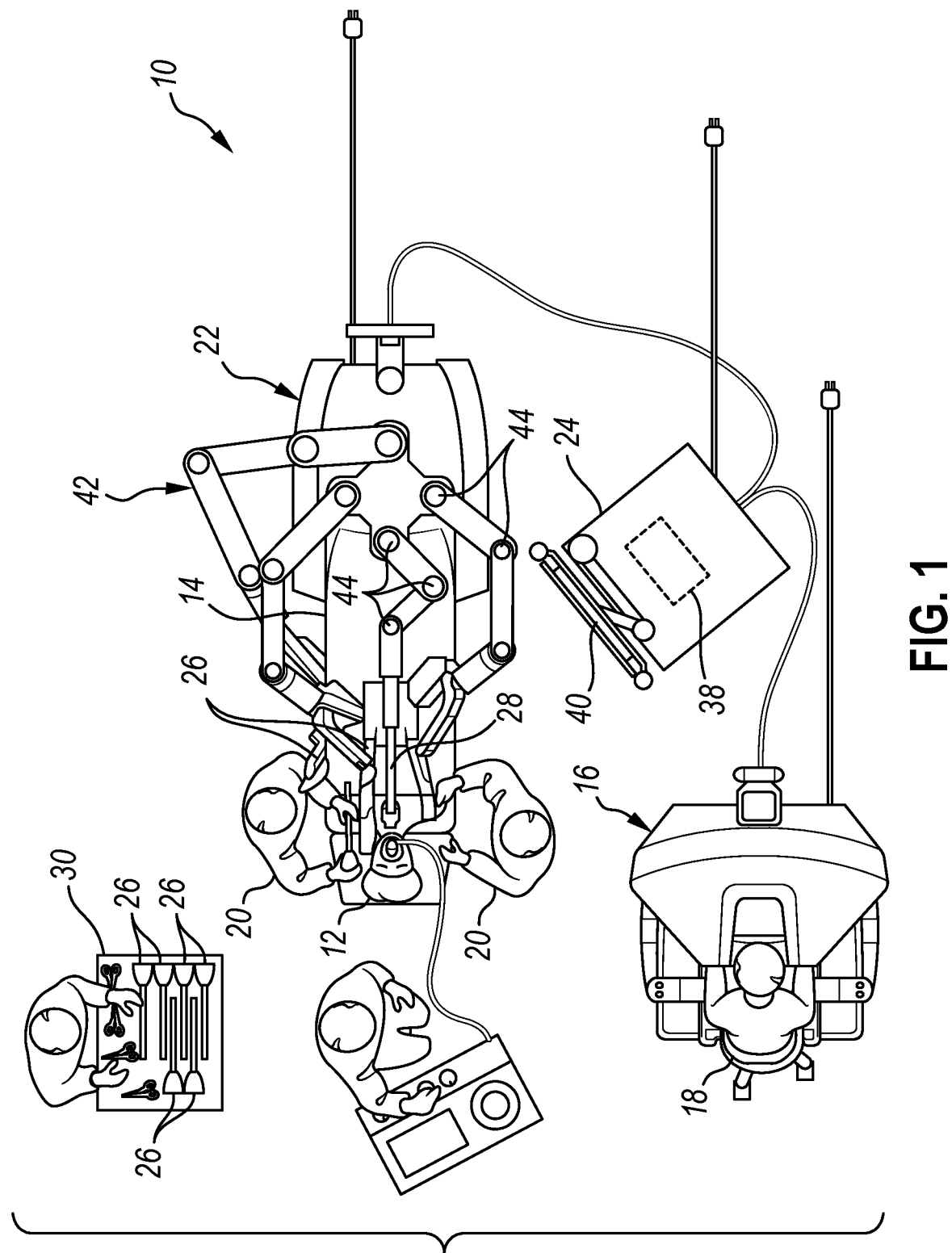
FIG. 1 depicts a top plan view of a robotic surgical system being used to perform a surgical procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "clockwise," "counterclockwise," "inner," "outer," "upper," "lower," and the like also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

I. Exemplary Robotic Surgical System

A. Overview

FIG. 1 shows a top plan view of an exemplary robotic surgical system (10) that may be used for performing a diagnostic or surgical procedure on a patient (12) who is lying down on an operating table (14). Robotic surgical system (10) may be constructed and operable in accordance with at least some of the teachings of U.S. Pat. No. 9,839,487, entitled "Backup Latch Release for Surgical Instrument," issued Dec. 12, 2017; U.S. Pat. No. 10,485,621, entitled "Sterile Barrier Between Surgical Instrument and Teleoperated Actuator," issued Nov. 26, 2019; U.S. Pat. No. 10,806,530, entitled "System and Method for Patient-Side Instrument Control," issued Oct. 20, 2020; U.S. Pat. No. 10,537,400, entitled "Detection Pins to Determine Presence of Surgical Instrument and Adapter on Manipulator," issued Jan. 21, 2020; U.S. Pat. No. 10,863,988, entitled "Surgical Instrument with Lockout Mechanism," published Dec. 15, 2020; U.S. Pat. No. 10,610,313, entitled "Surgical Instrument with Shiftable Transmission," issued Apr. 7, 2020; U.S. Pub. No. 2018/0271608, entitled "Manual Release for Medical Device Drive System," published Sep. 27, 2018; U.S. Pub. No. 2018/0325606, entitled "Systems and Methods for Operating an End Effector," published Nov. 15, 2018; U.S. Pub. No. 2019/0200989, entitled "Stapler Reload Detection and Identification," published Jul. 4, 2019; U.S. Pub. No. 2019/0239967, entitled "Stapler Beam Architecture," published Aug. 8, 2019; U.S. Pub. No. 2019/0262088, entitled "Robotic Surgical Stapler Assembly Configured to Use Stapler Reload," published Aug. 29, 2019; U.S. Pub. No. 2019/0239877, entitled "Wrist Architecture," published Aug. 8, 2019; U.S. Pub. No. 2019/0201150, entitled "Push-Pull Surgical Instrument End Effector Actuation Using Flexible Tension Member," published Jul. 4, 2019; U.S. Pub. No. 2019/0282233, entitled "Stapler Cartridge With an Integral Knife," published Sep. 19, 2019; U.S. Pub. No. 2019/0262088, entitled "Robotic Surgical Stapler Assembly Configured to Use Stapler Reload," published Aug. 29, 2019; U.S. Pub. No. 2020/0138529, entitled "Locking System for Medical Device Drive System," published May 7, 2020; and/or U.S. Pub. No. 2020/0397430, entitled "Surgical Instrument With Lockout Mechanism," published Dec. 24, 2020. The disclosure of each of the above-cited U.S. Patents and U.S. Patent Publications is incorporated by reference herein in its entirety.

Robotic surgical system (10) may include a surgeon's console (16) for use by a surgeon (18) during a surgical procedure. One or more assistants (20) may also participate in the procedure. Robotic surgical system (10) may include a patient side cart (22) (i.e., a surgical robot) and an electronics cart (24). Patient side cart (22) may manipulate at least one surgical instrument (26) (also referred to as a "tool assembly" or "tool") through an incision in the body of patient (12) while surgeon (18) views the surgical site through surgeon's console (16). As will be described in greater detail below, surgical instrument(s) (26) and an imaging device (shown as an endoscope (28)) may be removably coupled with patient side cart (22). Electronics cart (24) may be used to process the images of the surgical site for subsequent display to the surgeon (18) through surgeon's console (16). Electronics cart (24) may be coupled with endoscope (28) and may include a processor (38) (shown schematically) to process captured images for subsequent display, such as to surgeon (18) on the surgeon's console (16), on a display (40) of electronics cart (24), or another suitable display located locally and/or remotely. The images may also be processed by a combination of electronics cart (24) and processor (38), which may be coupled together to process the captured images jointly, sequentially, and/or combinations thereof. Electronics cart (24) may overlay the captured images with a virtual control interface prior to displaying combined images to the surgeon (18) via surgeon's console (16).

Figure 2:
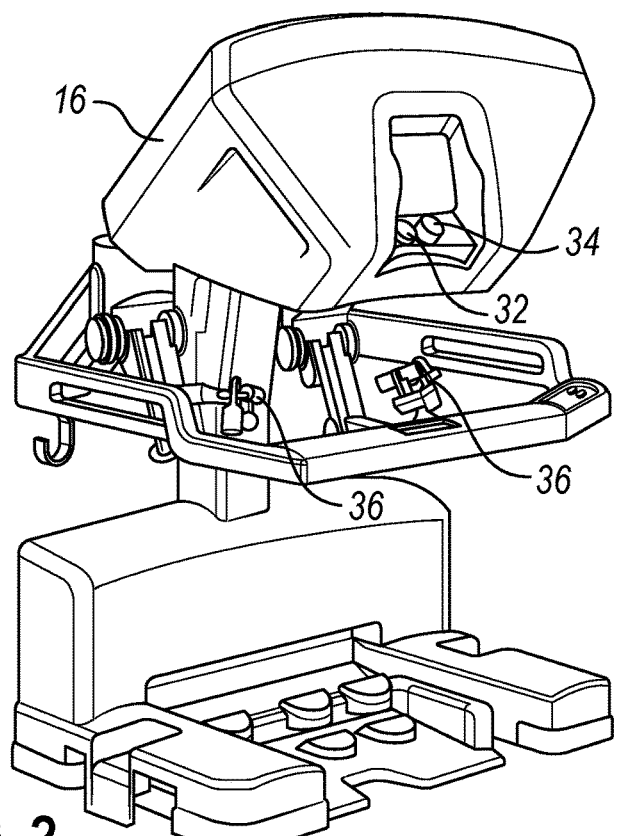
FIG. 2 depicts a perspective view of a surgeon's control console of the robotic surgical system of FIG. 1.

FIG. 2 shows a perspective view of surgeon's console (16). Surgeon's console (16) includes a left eye display (32) and a right eye display (34) for presenting surgeon (18) with a coordinated stereo view of the surgical site that enables depth perception. Surgeon's console (16) includes one or more input control devices (36) causing patient side cart (22) (shown in FIG. 1) to manipulate one or more surgical instruments (26). Input control devices (36) may provide the same degrees of freedom as their associated surgical instruments (26) (shown in FIG. 1) to provide surgeon (18) with telepresence, or the perception that the input control devices (36) are integral with surgical instruments (26). To this end, position, force, and tactile feedback sensors (not shown) may be employed to transmit position, force, and tactile sensations from surgical instruments (26) back to the surgeon's hands through input control devices (36). In some instances, surgeon's console (16) may be located in the same room as the patient so that surgeon (18) may directly monitor the procedure, be physically present if necessary, and speak to an assistant directly rather than over the telephone or other communication medium. Alternatively, surgeon (18) may be located in a different room, a completely different building, or other remote location from the patient allowing for remote surgical procedures.

Figure 3:
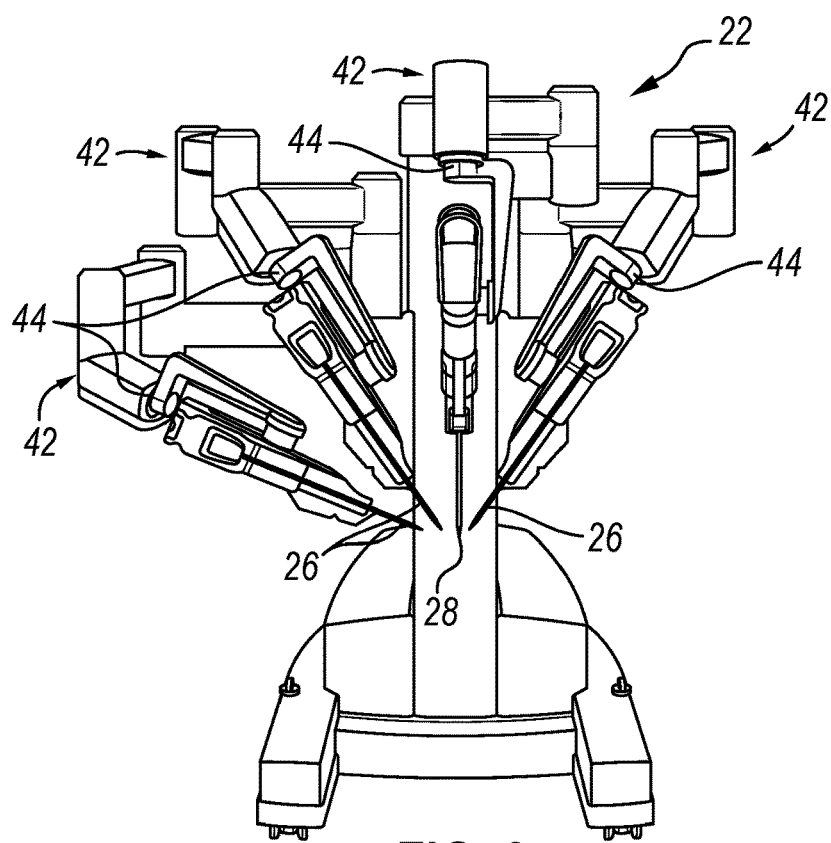
FIG. 3 depicts a front elevation view of a patient side cart of the robotic surgical system of FIG. 1.

FIG. 3 shows patient side cart (22) that manipulates surgical instruments (26). An image of the surgical site may be obtained by endoscope (28), which may include a stereoscopic endoscope. Manipulation is provided by robotic mechanisms, shown as robotic arms (42) that include at least one robotic joint (44) and an output coupler (not shown) that is configured to removable secure surgical instrument (26) with robotic arm (42). Endoscope (28) and surgical tools (26) may be positioned and manipulated through incisions in the patient so that a kinematic remote center is maintained at the incision to minimize the size of the incision. Images of the surgical site may include images of the distal ends of the surgical instruments (26) when they are positioned within the field-of-view of the endoscope (28). Patient side cart (22) may output the captured images for processing outside electronics cart (24). The number of surgical instruments (26) used at one time will generally depend on the diagnostic or surgical procedure and the space constraints within the operating room, among other factors. To change one or more of surgical instruments (26) being used during a procedure, assistant(s) (20) may remove surgical instrument (26) from patient side cart (22) and replace surgical instrument (26) with another surgical instrument (26) from a tray (30) (shown in FIG. 1) in the operating room.

B. Exemplary Surgical Instrument

Figure 4:
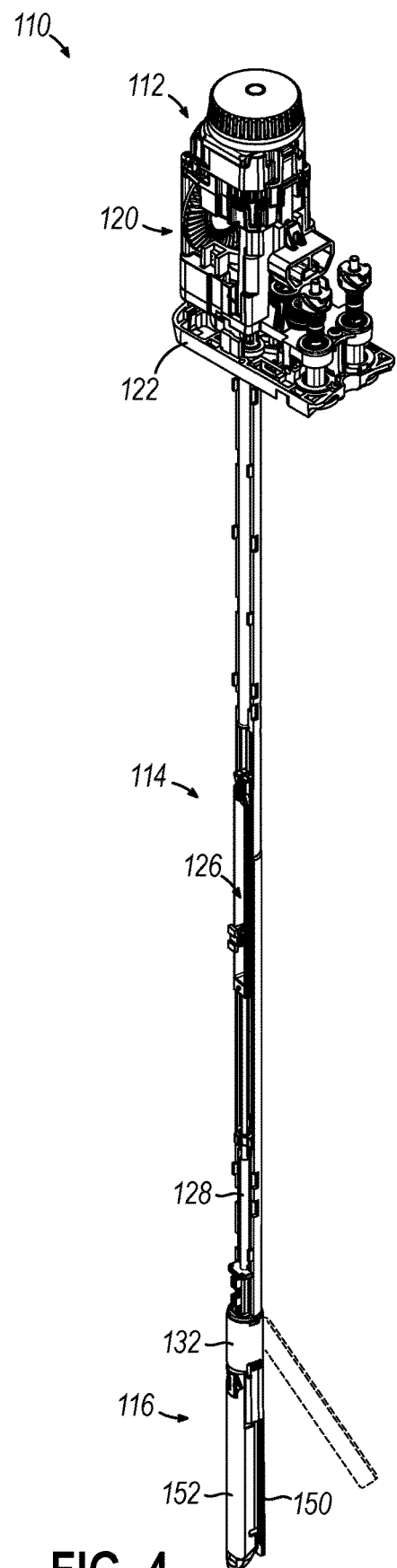
FIG. 4 depicts a perspective view of an exemplary surgical instrument that may be used with the robotic surgical system of FIG. 1, where the surgical instrument includes an instrument base, an elongate shaft, and an end effector, with select portions of the surgical instrument omitted to reveal internal features.
Figure 5:
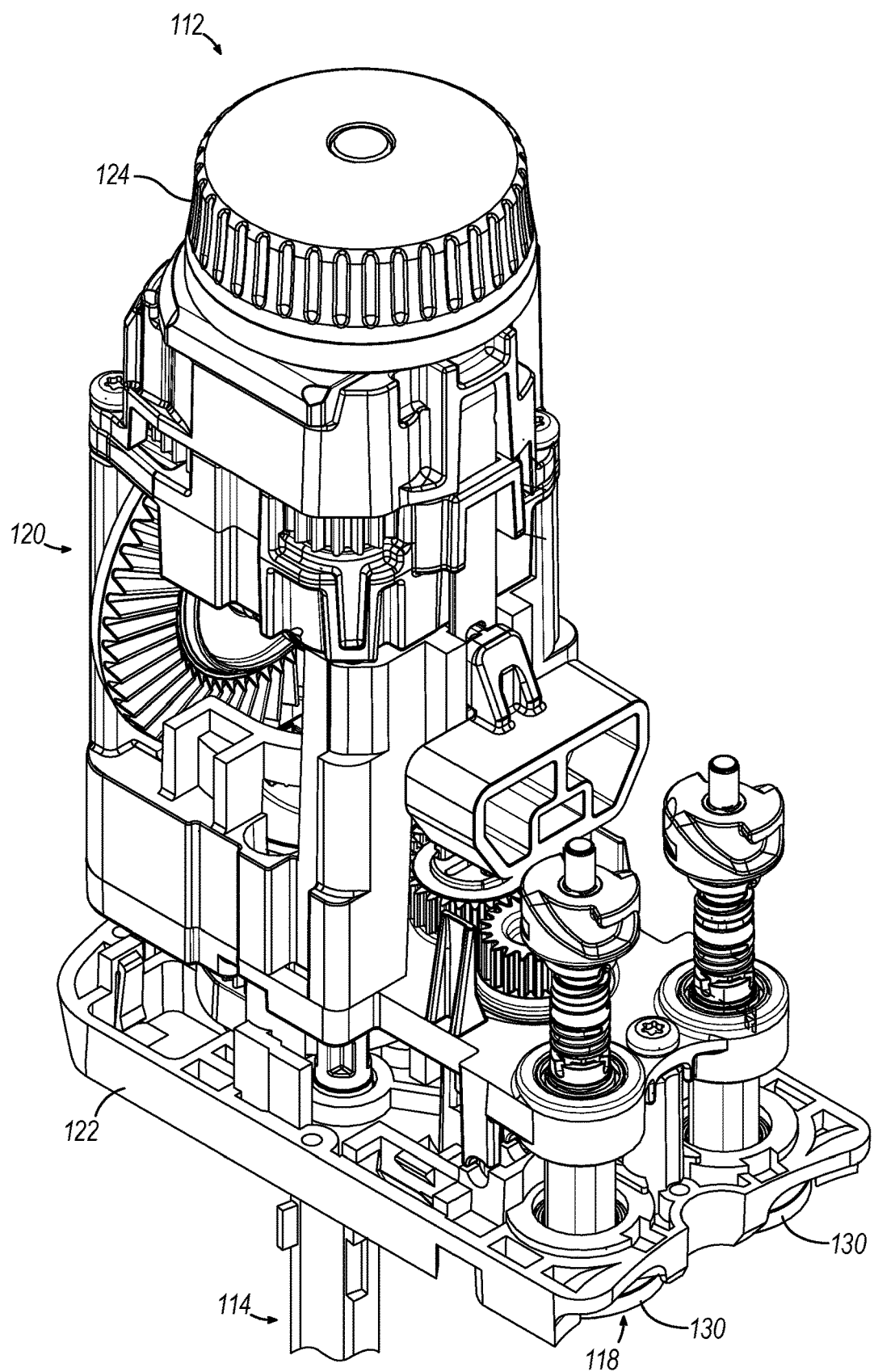
FIG. 5 depicts an enlarged perspective view of the instrument base of the surgical instrument of FIG. 4, with an outer housing omitted to reveal internal features.

FIGS. 4-5 show an exemplary surgical instrument (110) that may be mounted on and used with patient side cart (22)

shown in FIG. 3. Surgical instrument (110) can have any of a variety of configurations capable of performing one or more surgical functions. As shown, surgical instrument (110) includes an instrument base (112), a shaft assembly (114) extending distally from instrument base (112), and an end effector (116) at a distal end of shaft assembly (114). Instrument base (112) includes an attachment interface (118) that includes input couplers (130) that are configured to interface with and be driven by corresponding output couplers (not shown) of robotic arm (42) of patient side cart (22).

FIG. 5 shows an enlarged perspective view of instrument base (112) of surgical instrument (110). Instrument base (112) includes a drive system (120) mounted on a chassis (122) and having one or more actuators for actuating end effector (116) to clamp, staple, and cut tissue, and for articulating end effector (116) relative to a longitudinal axis defined by shaft assembly (114). Drive system (120) may include a manual actuator (124), which is shown in the form of a knob configured to be manually rotated. Manual actuator (124) may engage other components of surgical instrument (110) to serve as a "bailout" mechanism to obtain a desired movement in end effector (116) without powered actuation of drive system (120). Shaft assembly (114) may include additional drive components, such as portions of a drive train (126), that may couple instrument base (112) to a moveable feature (128) of shaft assembly (114) that may be coupled to end effector (116). Shaft assembly (114) may be configured for use with a variety of interchangeable end effectors (116), such as a cutter, grasper, a cautery tool, a camera, a light, or a surgical stapler, for example.

C. First Exemplary End Effector

Figure 6:
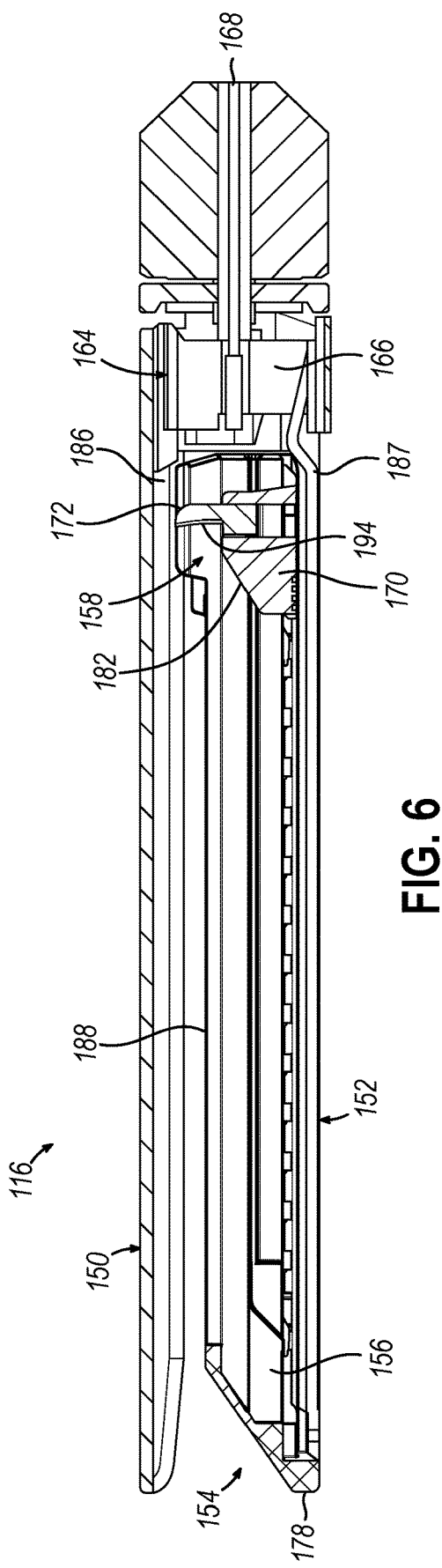
FIG. 6 depicts a side cross-sectional view of the end effector of FIG. 4, where the end effector includes a staple cartridge.

FIG. 6 shows a cross-sectional side view of end effector (116) of surgical instrument (110). End effector (116) extends distally from a distal end of shaft assembly (114). In the present example, end effector (116) comprises a surgical stapler, which may also be referred to herein as an "endocutter," configured to clamp, cut, and staple tissue. As illustrated, end effector (116) includes opposing upper and lower jaws (150, 152) configured to move relative to one another between open and closed positions for clamping and releasing tissue.

One or both of upper and lower jaws (150, 152) may be configured to pivot and thereby actuate end effector (116) between open and closed positions. Lower jaw (152) includes a removable staple cartridge (154). In the illustrated example, lower jaw (152) is pivotable relative to upper jaw (150) to move between an open, unclamped position and a closed, clamped position. In other examples, upper jaw (150) may move relative to lower jaw (152) (e.g., similar to end effector (210) of FIGS. 9-10). In still other examples, both and upper and lower jaws (150, 152) may move to actuate end effector (116) between open and closed positions. In the present example, lower jaw (152) is referred to as a "cartridge jaw" or "channel jaw," and upper jaw (150) is referred to as an "anvil jaw."

Figure 8:
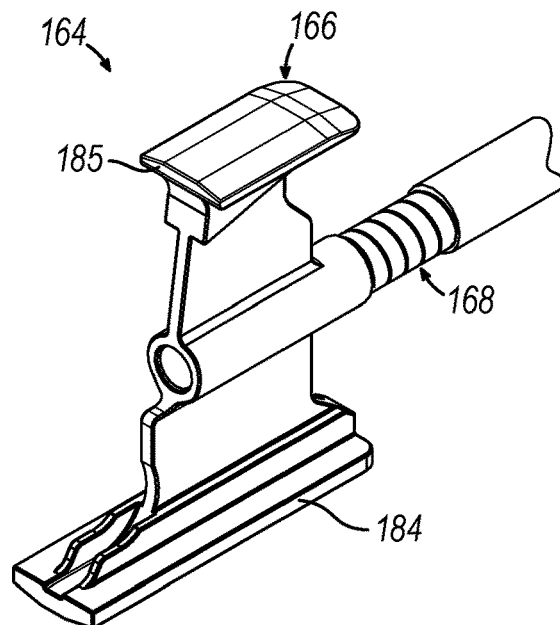
FIG. 8 depicts a driving assembly configured for use with the staple cartridge of FIG. 7.
Figure 9:
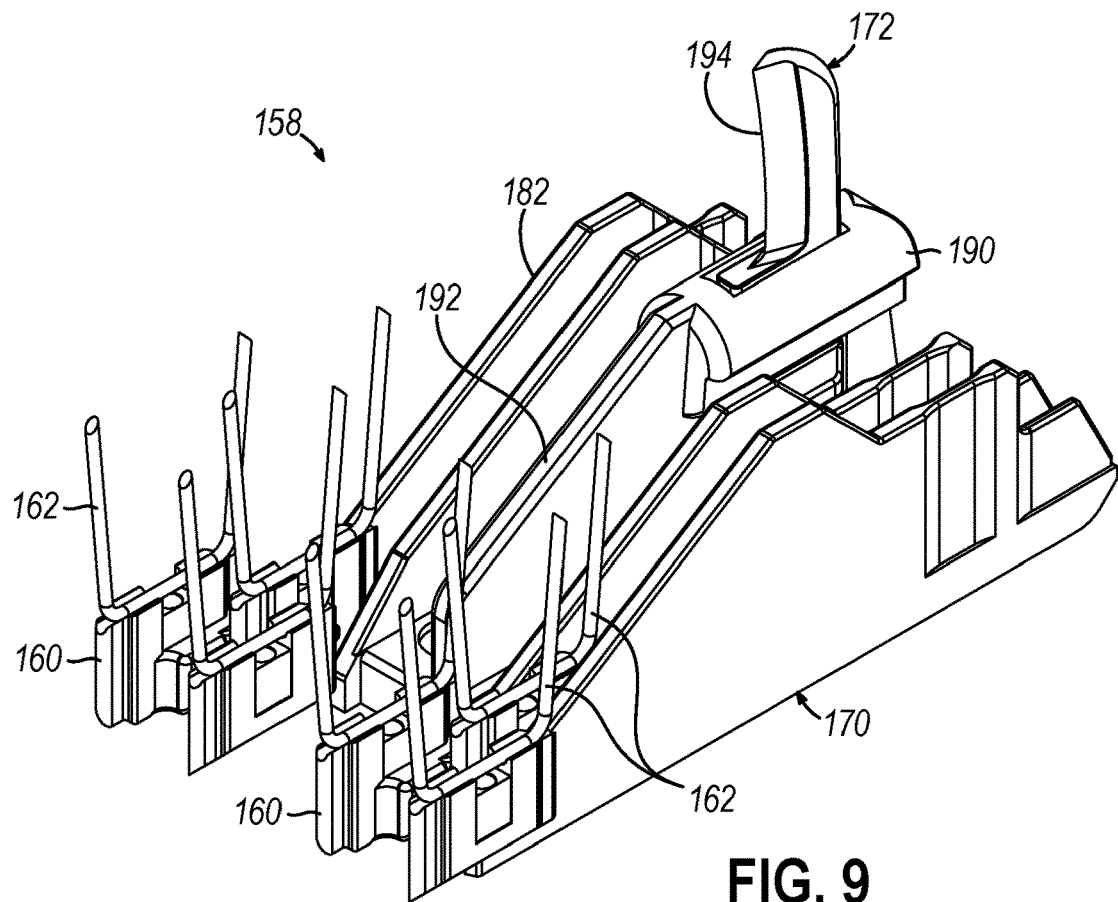
FIG. 9 depicts a firing assembly, staple drivers, and staples configured for use with the staple cartridge of FIG. 7.

Upper jaw (150) defines a surface that has a plurality of pockets (not shown) and operates as an anvil to deform staples ejected from staple cartridge (154) during operation. Staple cartridge (154) is replaceable, for example, by removing a used staple cartridge (154) from end effector (116) and inserting a new staple cartridge (154) into lower jaw (152). Staple cartridge (154) includes a staple cartridge body (156) that houses a firing assembly (158), a plurality of staple drivers (160) (also referred to as staple pushers), and a plurality of staples (162). As shown in FIGS. 6 and 8, end effector (116) includes a driving assembly (164) that includes a pusher member (166) that is operatively coupled with an actuation mechanism via a push rod (168). As shown in FIG. 6 and FIG. 9, firing assembly (158) includes a wedge sled (170) (also referred to as a staple pushing shuttle), and a knife member (172).

Figure 7:
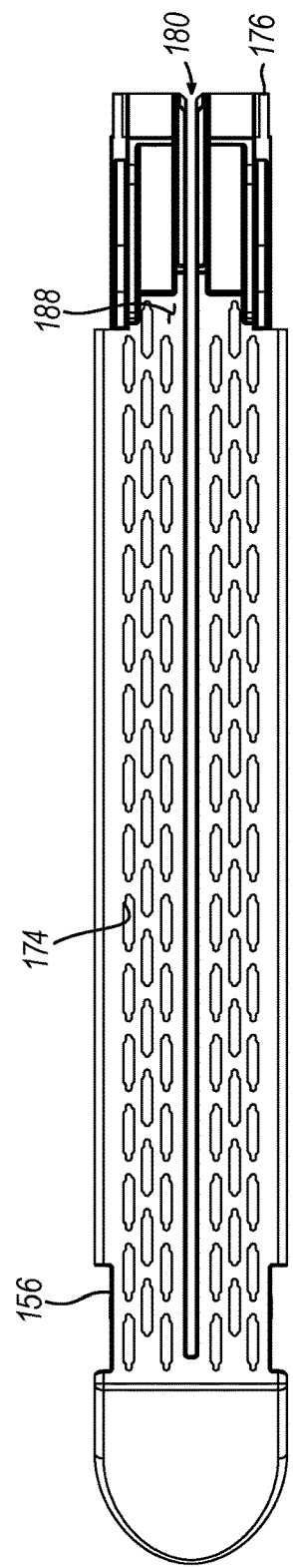
FIG. 7 depicts a top view of a deck of the staple cartridge of FIG. 6.

FIG. 7 shows atop view of staple cartridge body (156). Staple cartridge body (156) includes an array of staple accommodating apertures (174) (also known as openings) extending through an upper deck (188) of staple cartridge body (156). Each aperture (174) slidably houses a respective staple (162) in an unformed state and a free end of a corresponding staple driver (160) positioned beneath the unformed staple (162). Staple cartridge (154) includes proximal and distal ends (176, 178). In operation, staples (162) are sequentially deployed from apertures (174) by staple drivers (160) starting at proximal end (176) and advancing toward distal end (178). A vertical slot (180), configured to accommodate knife member (172), extends through part of staple cartridge (154).

FIG. 8 shows pusher member (166) as including first and second flanges (184, 185). First flange (184) is configured to be received in a longitudinal slot (186) (shown in FIG. 6) of upper jaw (150) and second flange (185) is configured to be received in a longitudinal slot (187) (shown in FIG. 6) of staple cartridge body (156) of lower jaw (152). First and second flanges (184, 185) move along longitudinal slots (186, 187) during actuation of pusher member (166). In some versions, pusher member (166) may include a single flange (e.g., omitting first flange (184)). As shown, longitudinal slot (186) is generally enclosed; and longitudinal slot (187) opens to an exterior surface of lower jaw (152).

FIG. 9 shows a perspective view of firing assembly (158), which is configured to be slidably received within the proximal end of staple cartridge body (156) in a longitudinal direction prior to engaging staple drivers (160) and staples (162). Wedge sled (170) of firing assembly (158) slidingly interfaces with staple cartridge body (156). More specifically, wedge sled (170) advances distally along staple cartridge body (156) such that ramp portions (182) of wedge sled contact staple drivers (160). Staple drivers (160) push staples (162) out of apertures (174) of staple cartridge body (156) to penetrate through and staple tissue clamped between staple cartridge body (156) and upper jaw (150). An initial distal actuation of pusher member (166) may move pusher member (166) into contact with wedge sled (170), with further actuation pushing staples (162) transversely out of staple cartridge body (156).

At an initial proximal position of wedge sled (170), knife member (172) is housed within staple cartridge body (156). The position of knife member (172) is controlled during a first portion of the movement of wedge sled (170) from proximal end (176) of staple cartridge body (156) to distal end (178) of staple cartridge (154), so that a cutting edge (194) of knife member (172) extends through vertical slot (180). Vertical slot (180) accommodates cutting edge (194) of knife member (172) as firing assembly (158) is moved toward distal end (178) of staple cartridge (154). Wedge sled (170) includes a guide member (190) that provides a bearing surface that cooperates with a similarly shaped surface of staple cartridge body (156) to guide wedge sled (170). Guide member (190) extends from a vertical rib member (192) of wedge sled (170), which forms a central portion of wedge sled (170). In some versions, knife member (172), or at least cutting edge (194), may be retracted below upper deck (188) of staple cartridge body (156) prior to firing assembly (158) reaching its distal most position adjacent to distal end (178) of staple cartridge (154).

D. Second Exemplary End Effector

Figure 10:
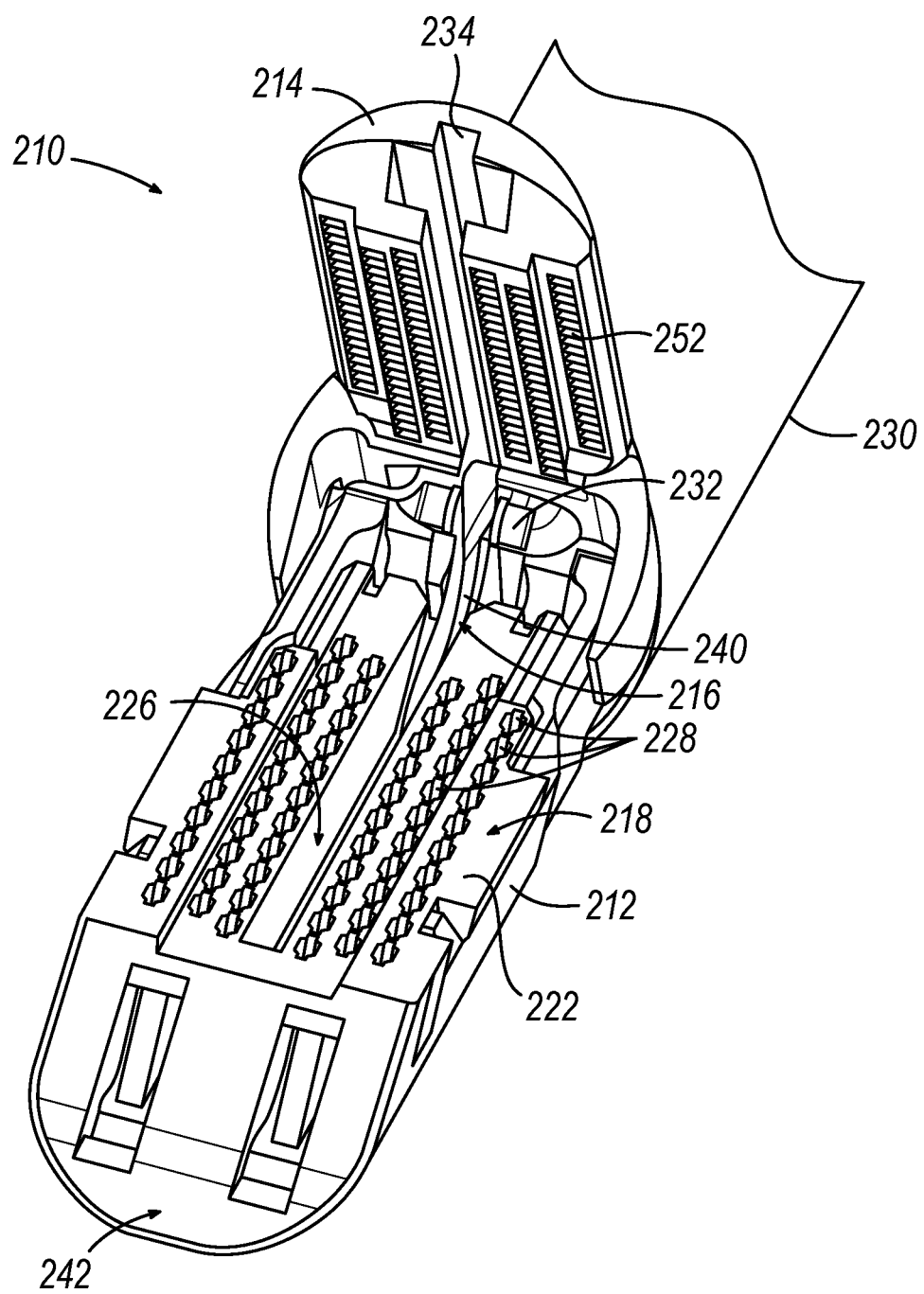
FIG. 10 depicts a second exemplary end effector that may be configured for use with the robotic surgical system of FIG. 1.
Figure 11:
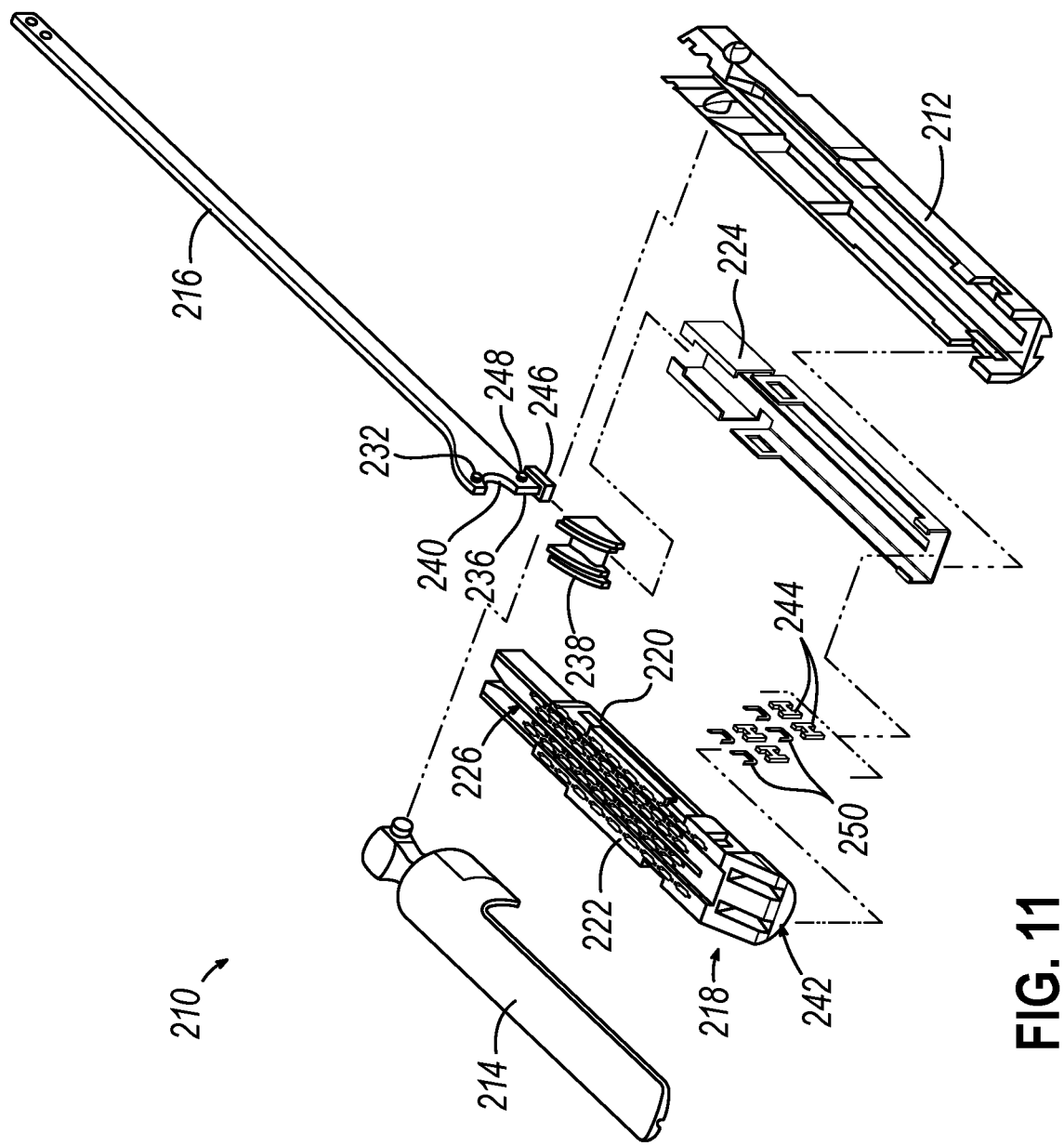
FIG. 11 depicts an exploded view of the end effector of FIG. 10.

FIGS. 10-11 show a second exemplary end effector (210), in an open position, that is configured to compress, cut, and staple tissue. End effector (210) may be configured for use with surgical instrument (110) of FIG. 4, or with surgical instruments of alternative constructions. End effector (210) may be constructed and operable in accordance with at least some of the teachings of U.S. patent application Ser. No. 16/916,295, entitled "Surgical Stapler Cartridge Retainer with Ejector Feature," filed Aug. 3, 2020, the disclosure of which is incorporated by reference herein in its entirety. End effector (210) of the present example includes a lower jaw (212) and an upper jaw in the form of a pivotable anvil (214). Lower jaw (212) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (214) may be constructed and operable in accordance with at least some of the teachings of U.S. Pat. No. 10,092,292, entitled "Staple Forming Features for Surgical Stapling Instrument," issued Oct. 9, 2018, the disclosure of which is incorporated by reference herein in its entirety.

FIG. 10 shows end effector (210), where anvil (214) is pivoted to an open position and a firing beam (216) is proximally positioned, allowing an unspent staple cartridge (218) to be removably installed into a channel of lower jaw (212). Staple cartridge (218) includes a cartridge body (220), which presents an upper deck (222) and is coupled with a lower cartridge tray (224). A vertical slot (226) is formed through part of staple cartridge (218) and opens upwardly through upper deck (222). One or more rows of staple apertures (228) are formed through upper deck (222) on one side of vertical slot (226), with one or more rows of staple apertures (228) being formed through upper deck (222) on the other side of vertical slot (226). End effector (210) is closed by distally advancing a closure tube (not shown) and a closure ring (230). Firing beam (216) is then advanced distally so that an upper pin (232) of firing beam (216) enters longitudinal anvil slot (234). Simultaneously, a pusher block (236) located at the distal end of firing beam (216) engages a wedge sled (238) housed within cartridge body (220), such that wedge sled (238) is pushed distally by pusher block (236) as firing beam (216) is advanced distally through staple cartridge (218) and anvil (214).

During firing, cutting edge (240) of firing beam (216) enters vertical slot (226) toward distal end (242) of staple cartridge (218), severing tissue clamped between staple cartridge (218) and anvil (214). As best seen in FIG. 11, wedge sled (238) presents inclined cam surfaces that urge staple drivers (244) upwardly as wedge sled (238) is driven distally through staple cartridge (218). A firing beam cap (246) slidably engages a lower surface of lower jaw (212). Wedge sled (238) is movable longitudinally within staple cartridge (218), while staple drivers (244) are movable vertically within staple cartridge (218). A middle pin (248) and pusher block (236) of firing beam (216) together actuate staple cartridge (218) by entering into vertical slot (226) within staple cartridge (218), driving wedge sled (238) distally into upward camming contact with staple drivers (244) that in turn drive staples (250) out through staple apertures (228) and into forming contact with staple forming pockets (252) on the inner surface of anvil (214). Additional examples of alternative surgical instruments and/or associated features are described in U.S. patent application Ser. No. 16/946,363, entitled "Articulation Mechanisms for Robotic Surgical Tools," filed on Jun. 18, 2020, the disclosure of which is hereby incorporated by reference herein in its entirety.

It will be appreciated that any one or more of the teachings described below may be combined with any one or more of the teachings described above in connection with FIGS. 1-11.

II. Exemplary Improvements to Jaw Closure Members

A. Exemplary Jaw Closure Member with Tapered Surfaces

As mentioned above, pusher member (166) includes flanges (184, 185) that may actuate within jaws (150, 152) in order to drive jaws (150, 152) toward and away from each other. In some instances, during actuation of pusher member (166) (see FIG. 8) in accordance with the description herein, a proximal or distal end of flanges (184, 185) may overly engage, bind against, or dig into portions of staple cartridge (154) and/or jaws (150, 152) defining associated longitudinal slots (186, 187). This over-engagement may cause surface irregularities on the portion of jaws defining channels, also referred to as slots (186, 187), which may increase the frictional resistance to advancing/retracing pusher member (166) within slots (186, 187) for future uses. The over-engagement and increase in frictional resistance to actuating pusher member (166) within slots (186, 187) may undesirably reduce the potential number of uses for instrument (110) with robotic surgical system (10). Therefore, it may be desirable to provide a pusher member (166) with features that may reduce the chances of over-engaging, or otherwise causing surface irregularities with, the portions of staple cartridge (154) and/or jaws (150, 152) defining longitudinal slots (186, 187).

Figure 12:
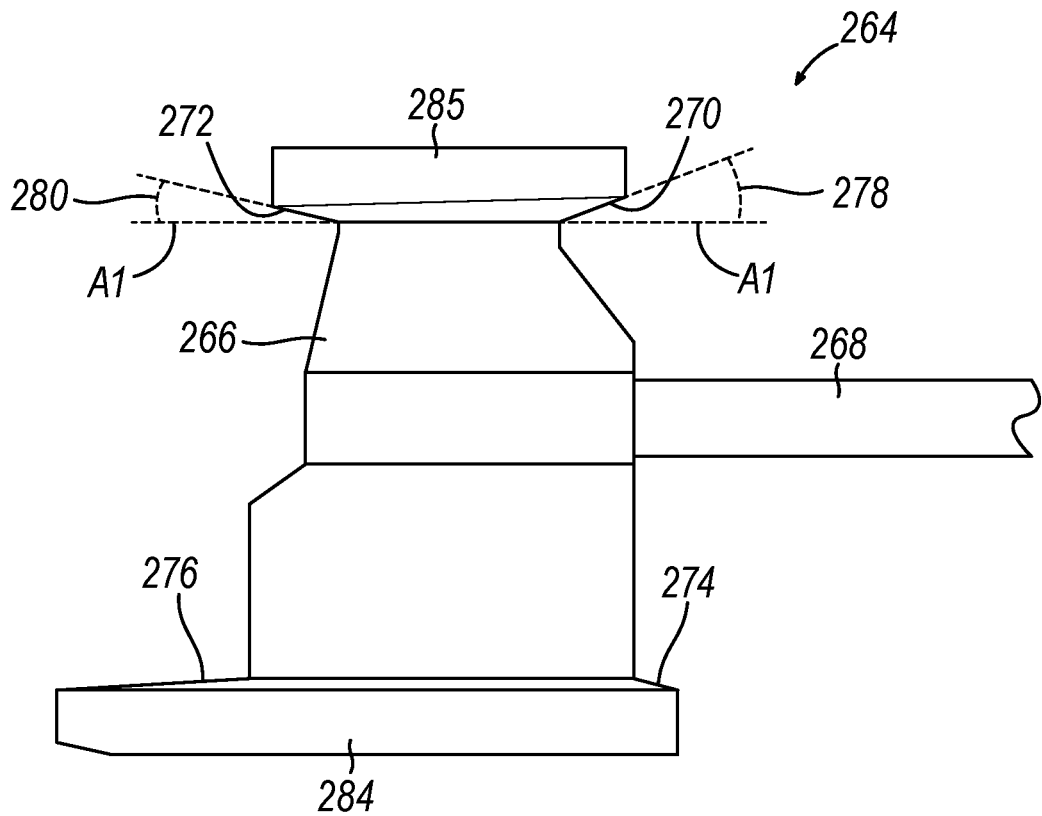
FIG. 12 depicts an elevational side view of an alternative driving assembly that may be readily incorporated into the end effector of FIG. 4.

FIG. 12 shows an exemplary alternative driving assembly (264) that may be readily incorporated into instrument (110) in replacement of driving assembly (164) described above. Therefore, driving assembly (264) may be substantially similar to driving assembly (164) described above, with differenced elaborated below.

Driving assembly (164) includes a pusher member (266) and a push rod (268). Push rod (268) is substantially similar to push rod (168) described above. Pusher member (266) is substantially similar to pusher member (166) described above, with difference elaborated below. Pusher member (266) includes first and second flanges (284, 285). First flange (284) is configured to be received in a longitudinal slot (187) (see FIGS. 13A-13E) of staple cartridge body (156) of lower jaw (152) and second flange (285) is configured to be received in a longitudinal slot (186) (see FIGS. 13A-13E) of upper jaw (150). First and second flanges (284, 285) may move within the confines of longitudinal slots (187, 186) during actuation of pusher member (266) in order to fire staples and sever tissue in accordance with the description herein.

Flanges (284, 285) include proximal facing tapered surfaces (274, 270) and distal facing tapered surfaces (276, 272), respectively. Proximal facing tapered surfaces (270, 274) extend proximally such that flanges (284, 285) decrease in width along the length of tapered surfaces (270, 274) in the proximal direction. Distal facing tapered surfaces (272, 276) extends distally such that flanges (284, 285) decrease in width in the distal direction along the length of tapered surfaces (272, 276) in the distal direction.

Tapered surfaces (270, 272, 274, 276) extend to define an angle with an axis extending parallel with the long axis of push rod (268). As exemplified with second flange (285), proximal facing tapered surface (270) defines a first angle (278) with a long axis (A1) that extends parallel with the long axis of push rod; while distal facing tapered surface (272) defines a second angle (280) with long axis (A1). First angle (278) may be greater than second angle (280).

Proximal facing tapered surfaces (270, 274) may have a steeper angle compared to distal facing tapered surfaces (282, 276), as the chance of pusher member (266) deforming the portions of upper jaw (150) and cartridge body (156) defining slots (186, 187) may be greater as pusher member (266) is retracted proximally after reaching a distal stopping point of the firing process.

Distal facing tapered surfaces (272, 276) are configured to cam against portions of upper jaw (150) and cartridge body (156) defining slots (186, 187) as pusher member (166) is driven distally; while proximal facing tapered surfaces (270, 274) are configured to cam against upper jaw (150) and cartridge body (156) defining slots (186, 187) as pusher member (166) is driven proximally. Due to the angles formed by tapered surfaces (270, 272, 274, 276), the portions of flanges (284, 285) in contact with upper jaw (150) and cartridge body (156) may be further away from the proximal and distal edges of flanges (284, 285), thereby reducing the chances of flanges (284, 285) digging into upper jaw (150) and staple cartridge (154). In other words, because tapered surfaces (270, 272, 274, 276) are angled, a portion of tapered surfaces (270, 272, 274, 276) may initiate contact with the portions of upper jaw (150) and cartridge body (156) defining slots (186, 187) in order to pivots jaws (150, 152), which be less likely to dig into, or otherwise deform the surfaces defining slots (186, 187) compared to a proximal or distal edge of flanges (284, 285).

Figure 13A:
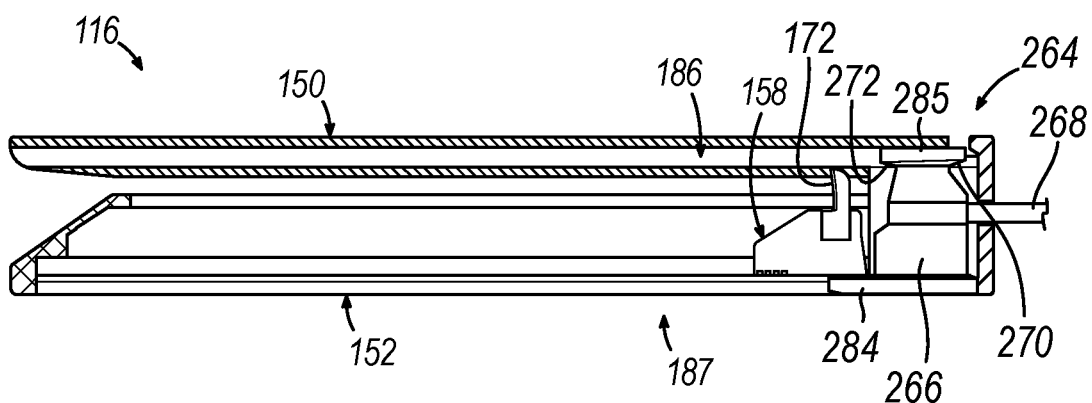
FIG. 13A depicts a cross-sectional side view of the driving assembly of FIG. 12 incorporated into the end effector of FIG. 4, taken along a centerline thereof, with the driving assembly in a pre-fired position.

FIGS. 13A-13E show an exemplary firing of driving assembly (264). First, as shown in FIG. 13A, driving assembly (264) may be in the pre-fired position. Push rod (268) may be driven distally to the position shown in FIG. 13B such that distal facing tapered surfaces (272, 276) cam against portions of upper jaw (150) and cartridge body (156) defining slots (186, 187). This interaction may be used to pivot jaws (150, 152) toward each other and grasp tissue. The angled nature of tapered surfaces (272, 276) may ensure a distal edge of flanges (284, 285) do not initiate contact between surfaces that cam against each other to pivot jaws (150, 152), which may reduce the chances of flanges (284, 285) digging into and damaging portions of upper jaw (150) and cartridge body (156) defining slots (186, 187).

Figure 13B:
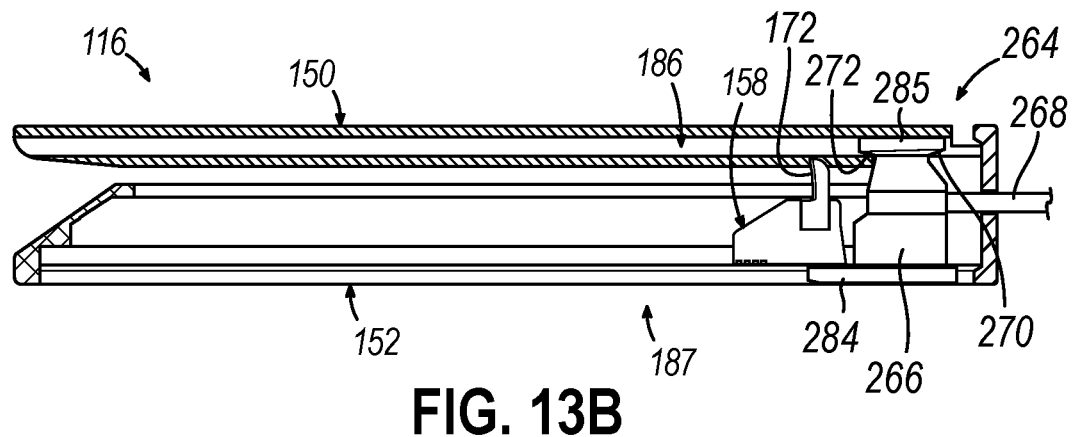
FIG. 13B depicts a cross-sectional side view of the driving assembly of FIG. 12 incorporated into the end effector of FIG. 4, taken along a centerline thereof, with the driving assembly in a partially advanced position.
Figure 13C:
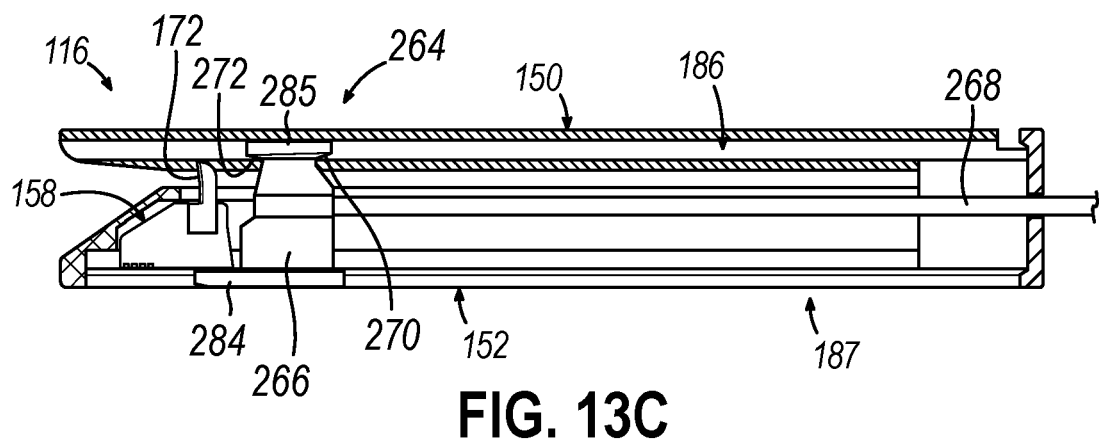
FIG. 13C depicts a cross-sectional side view of the driving assembly of FIG. 12 incorporated into the end effector of FIG. 4, taken along a centerline thereof, with the driving assembly in a fully advanced position.

Once the firing process starts, driving assembly (264) may be driven distally via movement of push rod (268) in order to staple and server tissue, as shown between FIGS. 13B-13C. It should be understood this distal movement may further pivot jaws (150, 152) toward each other via interaction between distal tapered surfaces (272, 276) and slots (186, 187), increasing the clamping force on tissue.

Figure 13D:
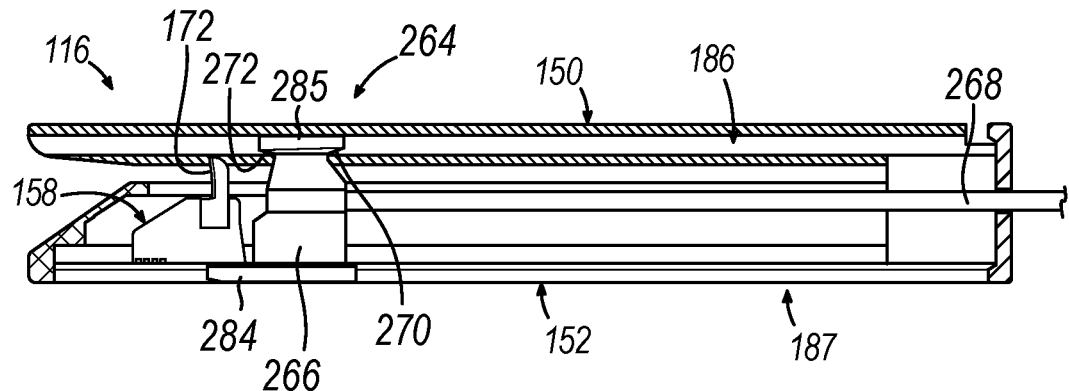
FIG. 13D depicts a cross-sectional side view of the driving assembly of FIG. 12 incorporated into the end effector of FIG. 4, taken along a centerline thereof, with the driving assembly initially retracted in the proximal direction from the fully advanced position.

With severing and stapling complete, push rod (268) may be driven proximally such that proximal facing tapered surfaces (270, 274) cam against portions of upper jaw (150) and cartridge body (156) defining slots (186, 187) to initially release tissue, as exemplified between FIGS. 13C-13D. The angled nature of tapered surfaces (270, 274) may ensure a proximal edge of flanges (284, 285) do not initiate contact between surfaces that cam against each other to pivot jaws (150, 152), which may reduce the chances of flanges (284, 285) digging into and damaging portions of upper jaw (150) and cartridge body (156) defining slots (186, 187).

Since distal movement of driving assembly (264) further clamps tissue between jaws (150, 152) the initial camming force between proximal facing tapered surfaces (270, 274) and slot (186, 187) may be greater to open jaws (150, 152) as compared to closing jaws (150, 152). Therefore, the steeper angle of proximal facings tapered surfaces (270, 274) as compared to distal facing tapered surfaces (272, 276) may be beneficial.

Figure 13E:
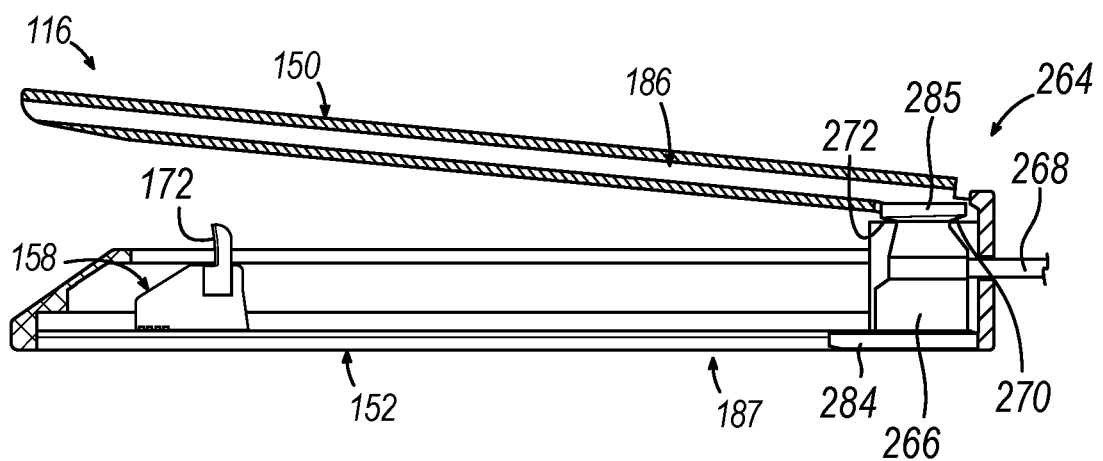
FIG. 13E depicts a cross-sectional side view of the driving assembly of FIG. 12 incorporated into the end effector of FIG. 4, taken along a centerline thereof, with the driving assembly fully retracted in the proximal direction from the fully advanced position.

With jaws (150, 152) initial pivoted open to release tissue, driving assembly (264) may then be driven to the pre-fired position as shown in FIG. 13E.

B. Exemplary Jaw Closure Member with Expandable Flange Members

As mentioned above, pusher member (166) is configured to actuate within jaws (150, 152) in order to drive jaws (150, 152) to close and open relative to each other and thereby grasp and release tissue. In particular, flanges (184, 185) of pusher member (166) abut against portions of staple cartridge (154) and/or jaws (150, 152) defining associated longitudinal slots (186, 187). When jaws (150, 152) grasp tissue, the tissue may impart a reactionary force onto jaws (150, 152). Such a reactionary force may attempt to drive jaws (150, 152) toward a more open position which may increase the frictional engagement between flanges (184, 185) and the portions of end effector (116) defining longitudinal slots (186, 187).

In some instances, if this frictional force between flanges (184, 185) and portions of end effector defining longitudinal slots (186, 187) becomes too great, flanges (184, 185) may overly engage or dig into portions of staple cartridge (154) and/or jaws (150, 152) defining associated longitudinal slots (186, 187), therefore inhibiting suitable movement of pusher number (166). With such suitable movement of driving assembly (164) being inhibited, an operator may have to (A) power robotic motor(s) (not shown) past a predetermined maximum power output level for a specific instrument (110) in order to move driving assembly (164), or (B) use manual actuator (124) to manually "bailout" end effector (116, 210), in order to retract driving assembly (164) back toward a proximal position. Use of robotic motor(s) (not shown) past a predetermined maximum power output level or use of manual actuator (124) to "bailout" instrument (110) may cause undesirable damage to instrument (110), thereby reducing the expected number of suitable uses of instrument (110), or even rendering instrument (110) unsuitable for further use.

Therefore, in instances where driving assembly (164) is inhibited from suitable movement to open and close jaws (150, 152) due to the frictional force between flanges (184, 185) and slots (186, 187) generated by the reactionary force of jaws (150, 152) grasping tissue, it may be desirable to allow flanges (184, 185) to selectively vertically expand relative to each other, thereby allowing jaws (150, 152) to slightly expand to thereby reduce the frictional force between flanges (184, 185) and slots (186, 187). Reducing the frictional force between flanges (184, 185) and slots (186, 187) may allow proximal retraction of pusher number (166) without use of robotic motor(s) (not shown) past a predetermined maximum power output level or use of manual actuator (124).

Figure 14:
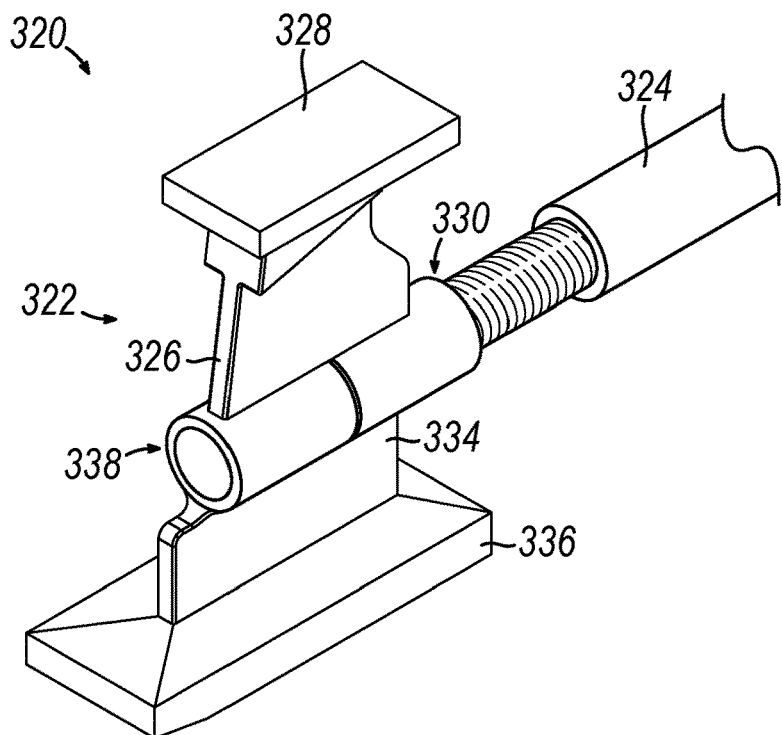
FIG. 14 depicts a perspective view of another alternative driving assembly that may be readily incorporated into the end effector of FIG. 4.
Figure 15A:
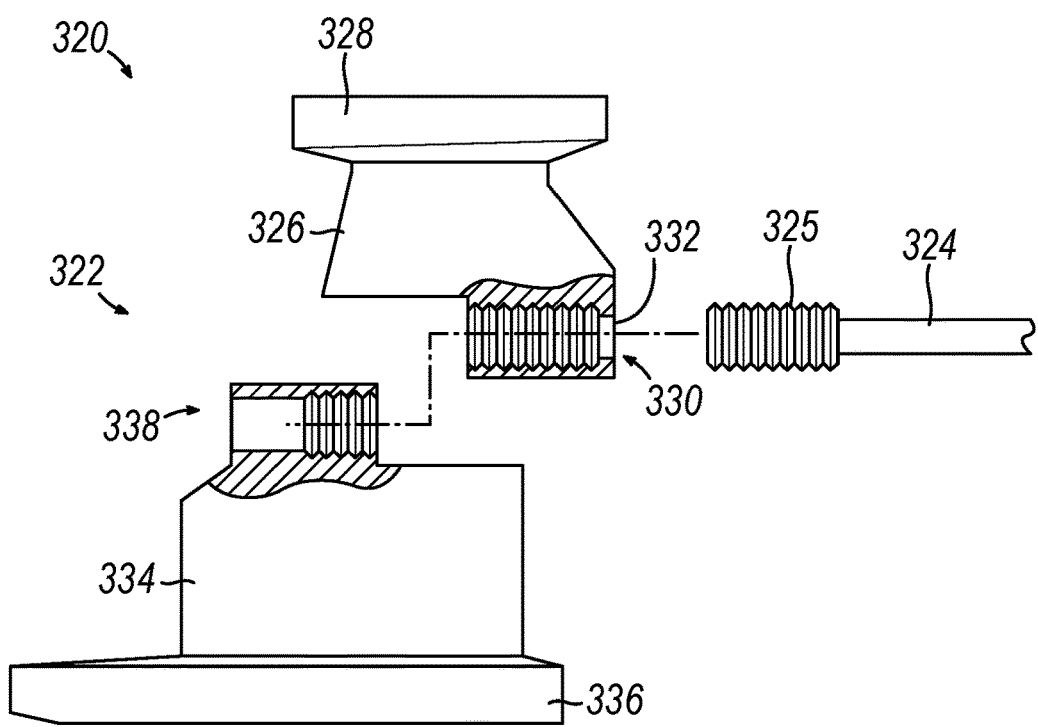
FIG. 15A depicts an exploded side view of the driving assembly of FIG. 14.
Figure 15B:
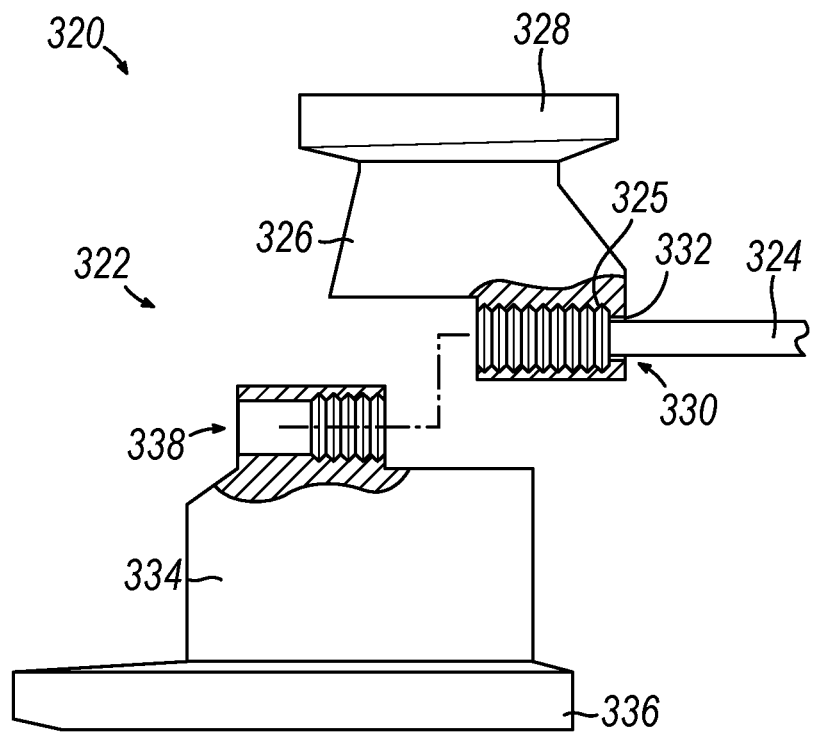
FIG. 15B depicts a side view of the driving assembly of FIG. 14, where a push rod is initially coupled to a first body of a pushing member.
Figure 15C:
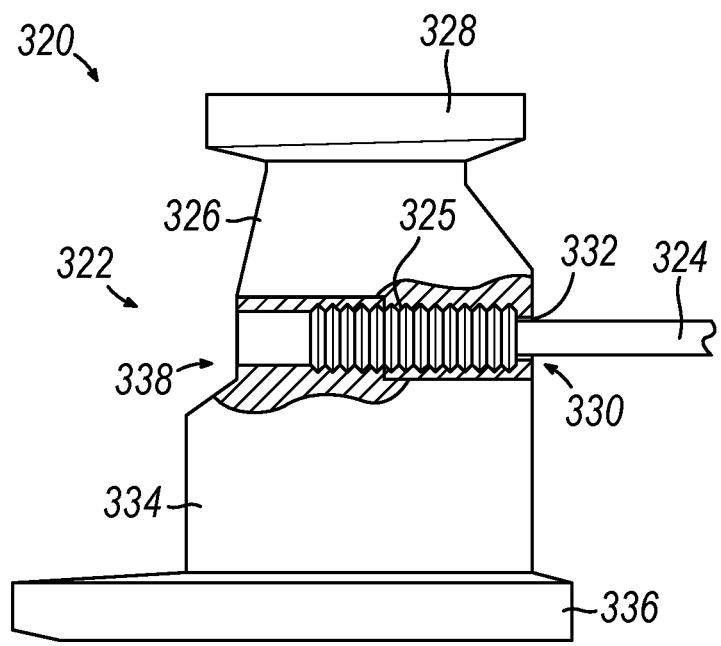
FIG. 15C depicts a side view of the driving assembly of FIG. 14, where the push rod of FIG. 15B is coupled to the first body of FIG. 15B, and where the first body is aligned with a second body of the pushing member.
Figure 15D:
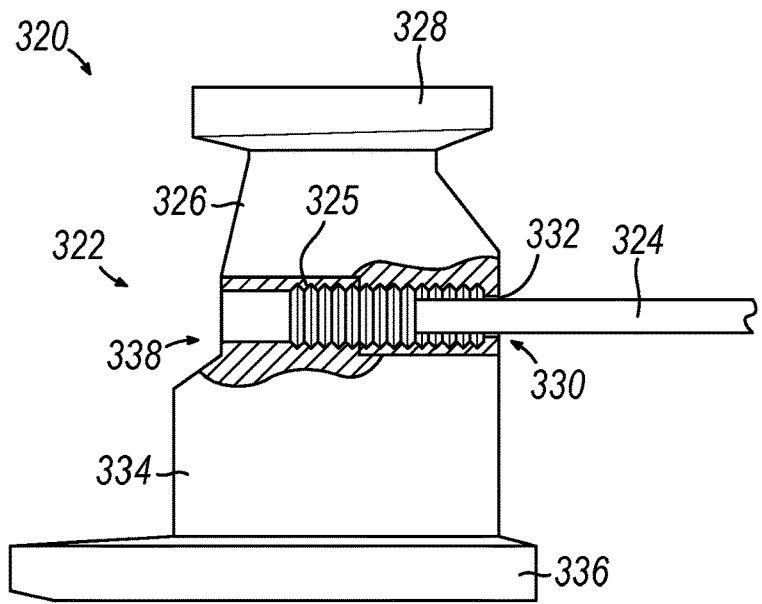
FIG. 15D depicts a side view if the driving assembly of FIG. 14 fully assembled.

FIGS. 14-15D show an exemplary driving assembly (320) that may be readily incorporated into instrument (110) for use with end effector (116) in replacement of driving assembly (164) described above. Therefore, driving assembly (320) may be substantially similar to driving assembly (164, 264) described above, with differences elaborated below.

As will be described in greater detail below, driving assembly (320) includes a pusher member (322) formed from two bodies (326, 334) each having a respective flange (328, 336) configured to (A) function substantially similar to flanges (184, 185) described above, and (B) selectively decouple from each other such that flanges (328, 336) may vertically actuate relative to each other. As will be described in greater detail below, since flange (328, 336) may selectively vertically actuate relative to each other, jaws (150, 152) may be allowed slightly expand to thereby reduce the frictional force between flanges (184, 185) and slots (186, 187) while grasping tissue. Therefore, in instances where suitable movement of driving assembly (320) is inhibited due to tissue imparting a reactionary force onto jaws (150, 152), flanges (328, 336) may expand to allow movement of at least a portion of pusher member (322) to release tissue without use of robotic motor(s) (not shown) past a predetermined maximum power output level or use of manual actuator (124).

Driving assembly (320) includes pusher member (322) and push rod (324), which are substantially similar to pusher member (166) and push rod (168) described above, with differences elaborated below. Push rod (324) includes a distal threaded portion (325) fixed that the distal end of push rod (324). Distal threaded portion (325) suitably meshes within threaded openings (330, 338) of bodies (326, 334) such that rotation of distal threaded portion (325) relative to bodies (326, 334) allows distal threaded portion (325) to translate relative to threaded openings (330, 338) when suitably coupled.

Pusher member (322) includes two bodies (326, 334) each having respective flanges (328, 336). Bodies (326, 334) also define a respective threaded opening (330, 338). Threaded openings (330, 338) are dimensioned to suitably align in order to both simultaneously mesh with distal threaded portion (325) of push rod (324). Therefore, distal threaded portion (325) of push rod (324) is configured to mesh with each threaded opening (330, 338) in order to couple first body (326) and second body (334) such that when coupled, push rod (324) may actuate bodies (326, 334) unitarily in order to open and close jaws (150, 152) in accordance with the description herein.

Push rod (324) may also rotate abouts its longitudinal axis in order to traverse a distance within threaded openings (330, 338). As will be described in greater detail below, if an operator desires to temporarily decouple first body (326) with second body (334), the operator may rotate push rod (324) (either manually or via robotic motors) such that distal threaded portion (325) only associated with first body (326), thereby allowing flanges (328, 336) to expand relative to each other. Body (332) also includes a proximal stop (332). Proximal stop (332) is configured to abut against distal threaded portion (325) after distal threaded portion (325) dissociates with threaded opening (338) of second body (334) in order to inhibit threaded portion (325) from accidentally decoupling with first body (326) as well. Therefore, proximal stop (332) acts to prevent distal threaded portion (325) from over rotating and proximally dissociating with first body (326).

FIGS. 15A-15D show an exemplary initial coupling of first body (326) with second body (334) utilizing distal threaded portion (325) of push rod (324). First, as shown between FIGS. 15A-15B, proximal end of push rod (324) may be fed through a distal opening of threaded opening (330) until distal threaded portion (325) is adjacent to threaded opening (330). Distal threaded portion (325) may be rotated in a first angular direction such that distal threaded portion (325) meshes with threaded opening (330). Distal threaded portion (325) may be rotated until a proximal end of distal threaded portion (325) engages stop (332), as shown in FIG. 15B.

Next, as shown in FIG. 15C, bodies (326, 334) may be positioned such that threaded openings (330, 338) are suitably aligned. With threaded openings (330, 338) aligned, flanges (328, 336) may be suitably positioned relative to each other in order to close and open jaws (150, 152) in accordance with the description herein. As shown between FIGS. 15C-15D, with threaded openings (330, 338) suitably aligned, distal threaded portion (325) may be rotated in a second angular direction, opposite the first angular direction, such that distal threaded portion longitudinally travels in the distal direction. Distal actuation of threaded portion (325) allows distal threaded portion (325) to suitably engage threaded opening (338) of second body (334), as shown in FIG. 15D. With distal threaded portion (325) suitably engaged with both bodies (326, 334), pusher member (322) and driving assembly (320) are assembled.

Figure 16A:
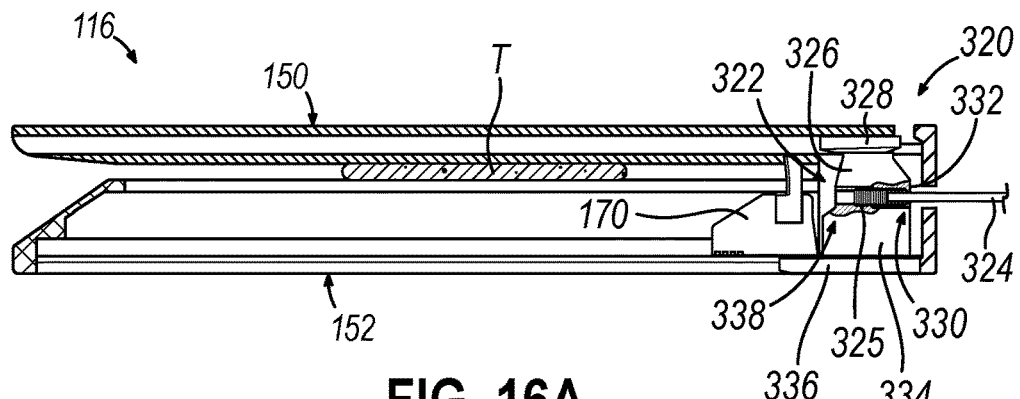
FIG. 16A depicts a cross-sectional side view of the driving assembly of FIG. 14 incorporated into the end effector of FIG. 4, where the driving assembly is in a pre-fired position.

FIGS. 16A-16G show an exemplary use of driving assembly (320) to attempt to sever and staple tissue (T), but then release tissue (T) before the firing process is fully completed. FIG. 16A shows tissue (T) grasped between jaws (150, 152) and driving assembly (320) in the pre-fired, proximal position. When the operator desires to sever and staple tissue in accordance with the description herein, the operator may initiate the firing process via surgeon's console (16) in accordance with the description herein.

Figure 16B:
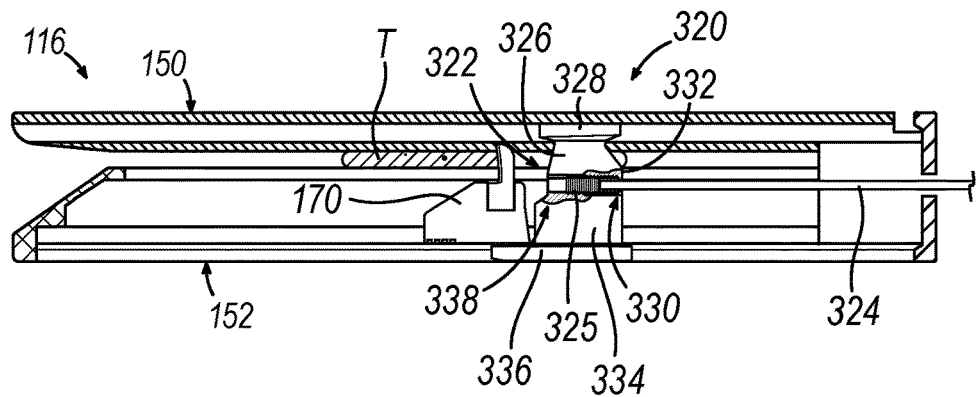
FIG. 16B depicts a cross-sectional side view of the driving assembly of FIG. 14 incorporated into the end effector of FIG. 4, where the driving assembly is advanced to a partially fired position.

As exemplified in FIGS. 16B, for any suitable reasons, it may be desirable to release tissue (T) before the firing process is complete. In some instances, tissue (T) may provide a reactionary force on jaws (150, 152) to thereby inhibit further distal translation of driving assembly (320) and/or proximal retraction of driving assembly (320). Therefore, it may be desirable to allow flanges (328, 336) to selectively expand vertically relative to each other, thereby reducing the frictional force between flanges (328, 336) and slots (186, 187) and allowing proximal retraction of first body (326) to release tissue (T) without use of robotic motor(s) (not shown) past a predetermined maximum power output level or use of manual actuator (124).

Figure 16C:
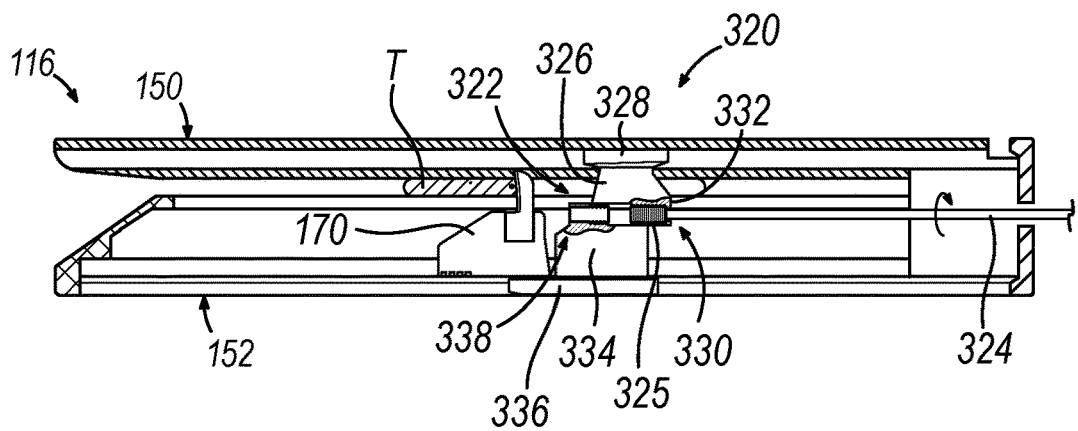
FIG. 16C depicts a cross-sectional side view of the driving assembly of FIG. 14 incorporated into the end effector of FIG. 4, where the driving assembly is advanced to a partially fired position and the first body of the pushing member is decoupled from the second body of the pushing member.

As shown between FIGS. 16B-16C, push rod (324) may be rotated such that distal threaded portion (325) disengages with threaded opening (338) of second body (334). Push rod (324) may be rotated manually or with robotic motor. With distal threaded portion (325) disengaged with second body (334), second body (334) and first body (326) may expand relative to each other, thereby allowing the reactionary force tissue (T) imparts on jaws (150, 152) to at least slightly expand jaws (150, 152) to reduce the frictional force between flanges (328, 336) and slots (186, 187).

Figure 16D:
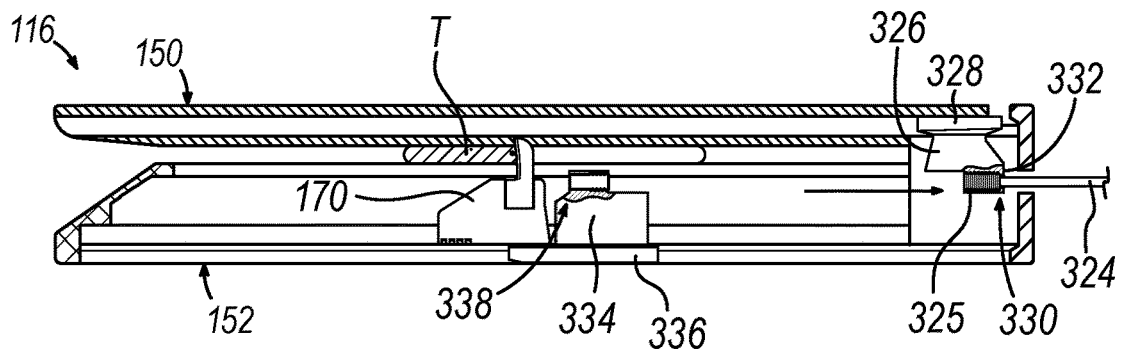
FIG. 16D depicts a cross-sectional side view of the driving assembly of FIG. 14 incorporated into the end effector of FIG. 4, where the first body of the pushing member is proximally retracted within the end effector.

Therefore, as shown between FIGS. 16C-16D, push rod (324) may proximally actuate such that first body (326) is returned to the pre-fired position, but such that second body (334) remains in the position shown in FIG. 16C. With the reduced frictional force between flanges (328, 336) and slots (186, 187), push rod (324) may be proximally retracted without use of robotic motor(s) (not shown) past a predetermined maximum power output level or use of manual actuator (124).

Figure 16E:
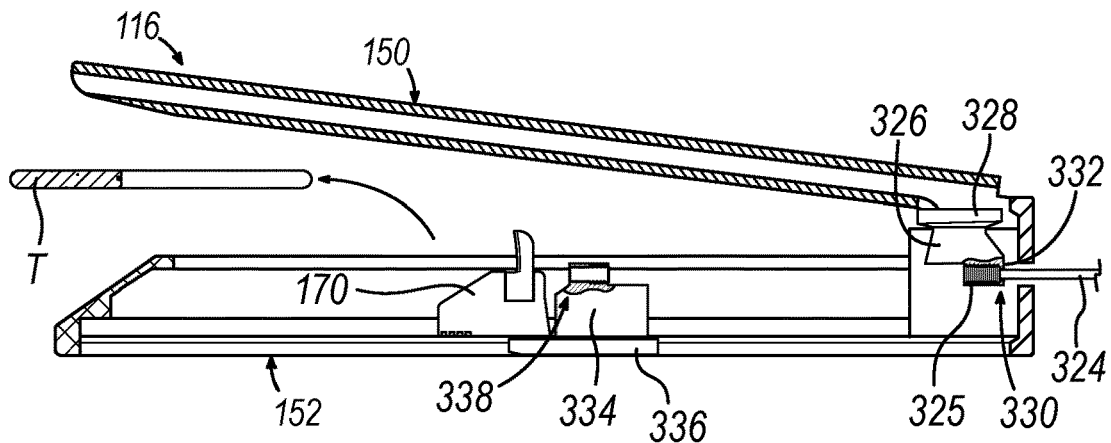
FIG. 16E depicts a cross-sectional side view of the driving assembly of FIG. 14 incorporated into the end effector of FIG. 4, where the first body of the pushing member is proximally retracted within the end effector and tissue is released from the jaws of the end effector.
Figure 16F:
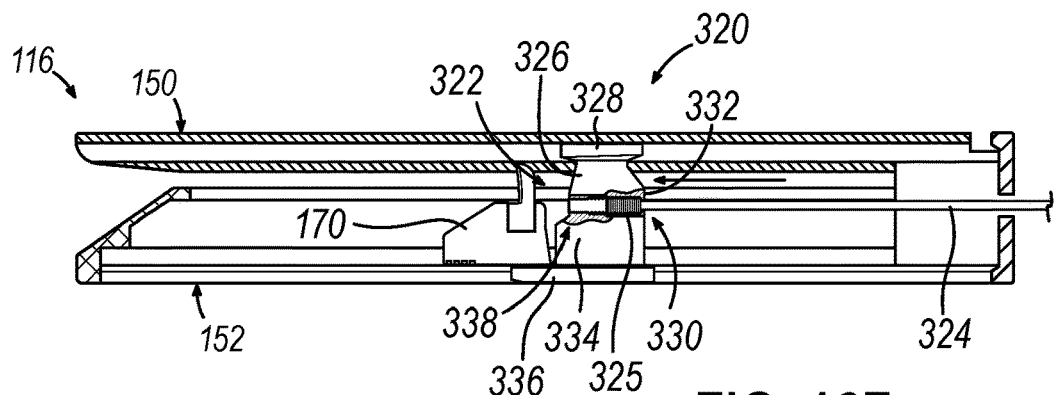
FIG. 16F depicts a cross-sectional side view of the driving assembly of FIG. 14 incorporated into the end effector of FIG. 4, where the first body of the pushing member is distally advanced to abut against the second body of the pushing member.
Figure 16G:
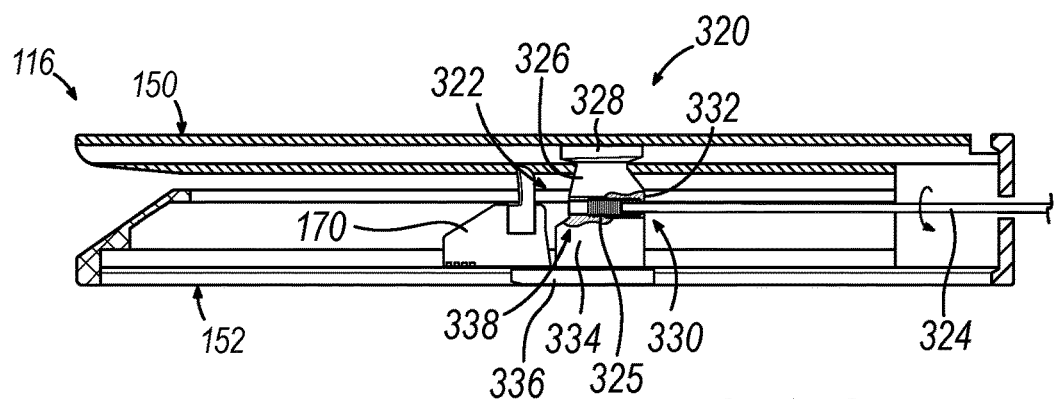
FIG. 16G depicts a cross-sectional side view of the driving assembly of FIG. 14 incorporated into the end effector of FIG. 4, where the first body of the pushing member is recoupled with the second body.

As shown in FIGS. 16E, jaws (150, 152) may open relative to each other in order to release grasped tissue (T) that has been partially stapled and severed. With tissue (T) released, push rod (324) may actuate first body (326) back against second body (334) such that threaded openings (330, 338) are aligned, as shown in FIG. 16F. Then, as shown in FIGS. 16G, push rod (324) may be rotated such that distal threaded portion (325) engages with threaded opening (338) of second body (334), thereby suitably recoupling first body (326) and second body (334). With bodies (326, 334)

recoupled, push rod (324) may be proximally retracted back to pre-fired position for the purposes of loading a new staple cartridge (154).

The decoupling and recoupling process described herein may be automatically initiated in response to certain conditions sensed by instrument (110). Any suitable conditions may initiate the decoupling and recoupling process as would be apparent to one skilled in the art in view of the teachings herein.

As mentioned above, after first body (326) and second body (334) are decoupled, push rod (324) may actuate first body (326) back against second body (334) such that threaded openings (330, 338) are aligned for purposes of recoupling distal threaded portion (325) with threaded opening (338) of second body (334). Therefore, it may be desirable to ensure the threaded openings (330, 338) are suitably aligned such that distal threaded portion (325) may suitably re-mesh with threaded opening (338) during the recoupling process.

Figure 17:
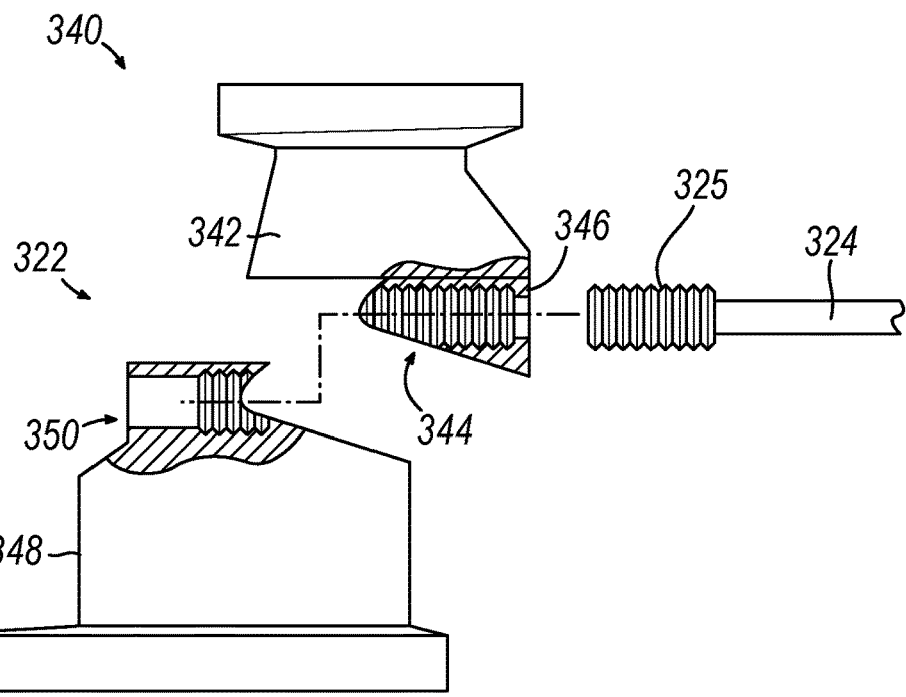
FIG. 17 depicts an exploded side view of another alternative driving assembly that may be readily incorporated into the end effector of FIG. 4.

FIG. 17 shows an exemplary pusher member (340) that may be readily incorporated into driving assembly (320) in replacement of pusher member (322) described above. Pusher member (340) may be substantially similar to pusher member (322) described above, with differences elaborated below. Therefore, pusher member (340) includes a first body (342) and a second body (348) defining a respective threaded opening (344, 450); which may be substantially similar to first body (326), second body (334), and threaded openings (330, 338) described above, with differences elaborated below.

In particular, threaded opening (344) of first body (342) includes an alignment protrusion (346); while second body (348) includes an alignment recess (352). Alignment protrusion (346) and alignment recess (352) are complementary such that as first body (342) is actuated to abut against second body (348), protrusion (346) and recess (352) interact with each other to suitably align threaded openings (344, 350). This suitable alignment dues to interaction between protrusion (346) and recess (352) may allow distal threaded portion (325) to more easily re-mesh with threaded opening (350) of second body (348). Additionally, the interaction between protrusion (346) and recess (352) may suitably space flanges of first body (342) and second body (348) such that jaws (150, 152) may close with an appropriate amount of closure force, even after first body (342) and second body (348) are recoupled in accordance with the description herein.

Figure 18:
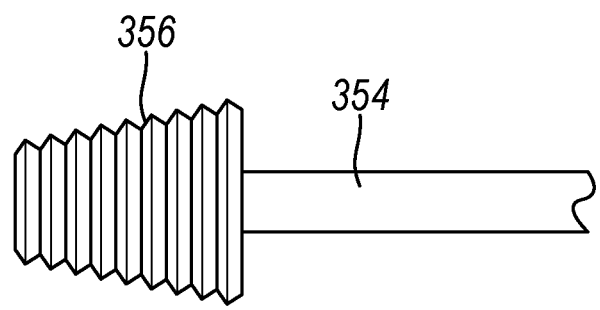
FIG. 18 depicts an elevation side view of an alternative push rod that may be readily incorporated into the driving assembly of FIG. 17.

FIG. 18 shows an alternate push rod (354) that may be used to promote alignment of threaded openings (330, 338). Push rod (354) may be substile similar to push rod (324) described above, except that push rod (354) includes a distal threaded portion (356) having a conical profile. The conical profile of distal threaded portion (356) may promote suitable alignment with first body (326) and second body (334) during the recoupling process in accordance with the description herein. It should be understood that in instances where distal threaded portion (356) is used, threaded openings (330, 338) may have a complementary shape to that of conical threaded portion (356) to promote suitable meshing between threads.

Figure 19:
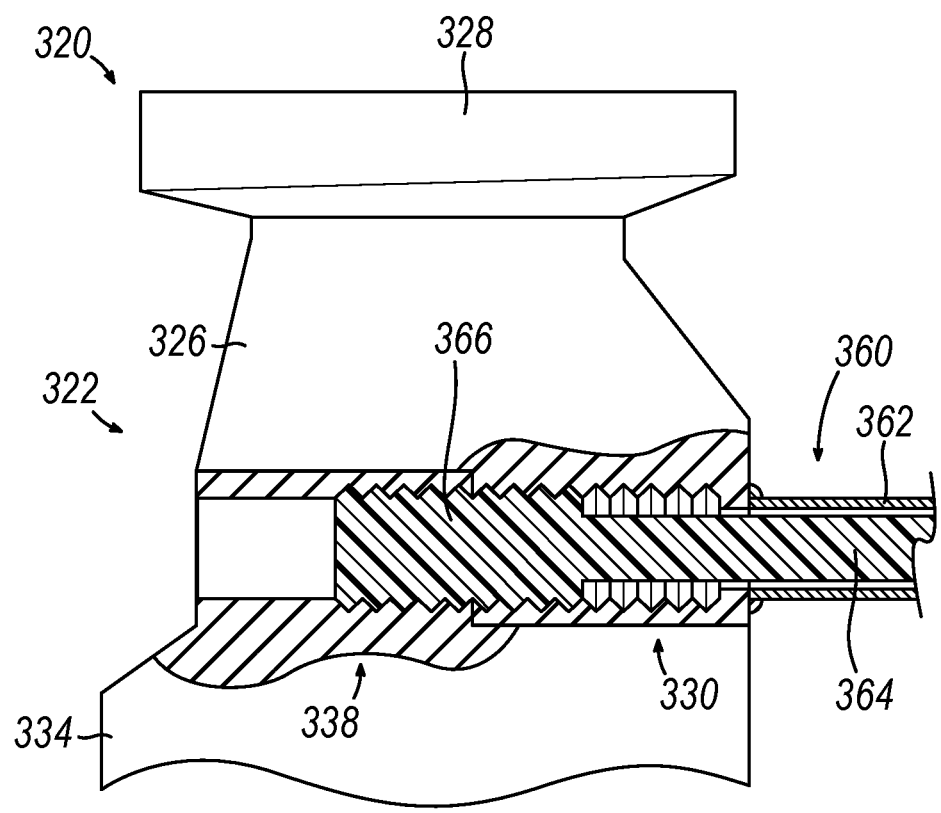
FIG. 19 depicts a cross-sectional side view of an alternative push rod assembly that is incorporated into the driving assembly of FIG. 14.

In some instances, it may be desirable to separate components of push rod (324) that (A) translate in order to fire staples and sever tissue, and (B) rotate in order to selectively allow flanges (328, 336) to expand relative to each other. FIG. 19 shows a push rod (360) having a translating member (362) fixed to first body (326), and a rotating member (364) rotatably disposed within translating member (362). Translating member (362) may be coupled to a robotic motor and configured to translate to drive translation of pusher member (322).

Rotating member (364) may include a distal threaded portion (366) which is substantially similar to distal threaded portion (325) described above. Rotating member may be attached to a manual bailout feature or may be coupled to another robotic motor configured to rotate distal threaded portion (325) in order to suitably decouple and recouple first body (326) with second body (334) in accordance with the description herein. Since rotating member (364) and translating member (363) are operable to function independent of each other, they may be coupled to separate driving components.

In some instances, it may be desirable to allow flanges (328, 336) to expand relative to each other, without having bodies (326, 334) completely disassociate with each other, as this may allow for simplification in recoupling bodies (326, 334) after releasing grasped tissue (T) that inhibits proximal translation of pusher member (322) in accordance with the description herein.

Figure 20:
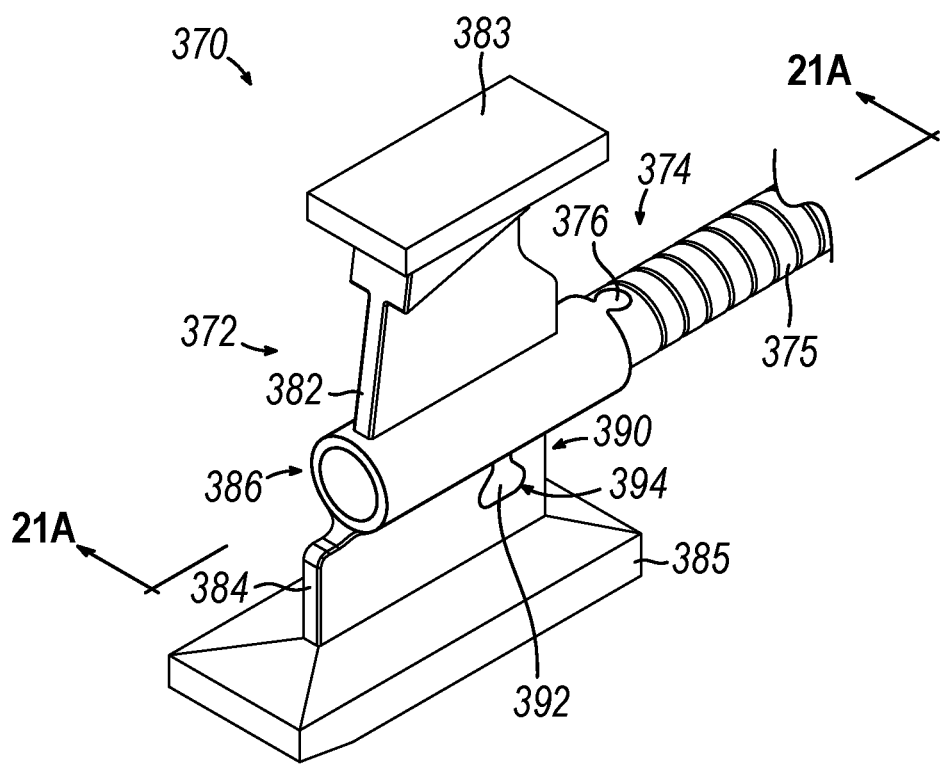
FIG. 20 depicts a perspective view of an alternative driving assembly that may be readily incorporated into the end effector of FIG. 4.
Figure 21A:
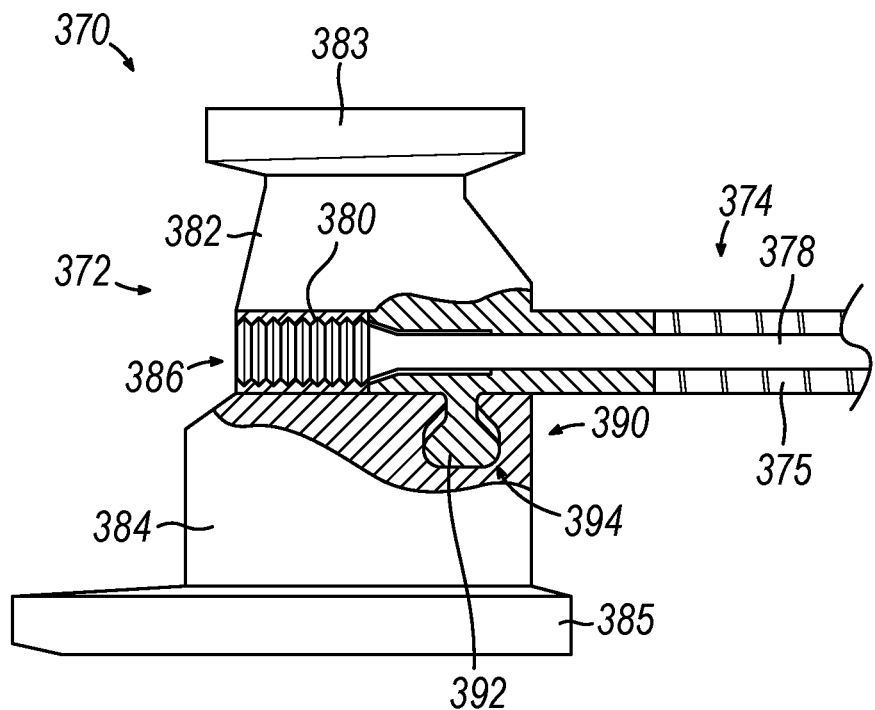
FIG. 21A depicts a partial cutaway side view of the driving assembly of FIG. 20 in a fully assembled position.
Figure 21B:
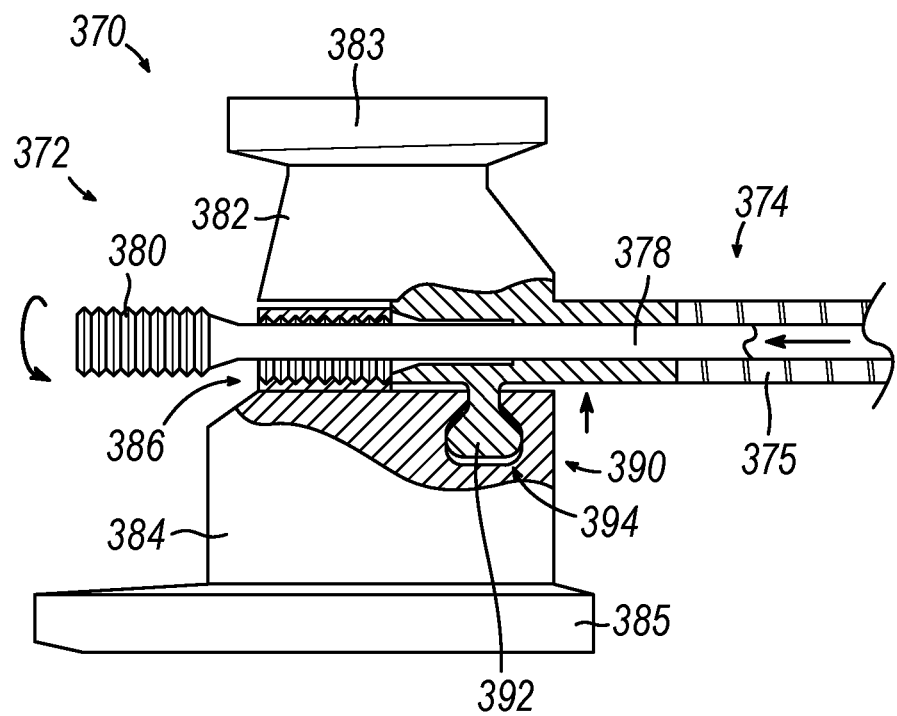
FIG. 21B depicts a partial cutaway side view of the driving assembly of FIG. 20 in a disassembled position.

FIGS. 20-21B show an exemplary driving assembly (370) that may be readily incorporated into instrument (110) in replacement of driving assembly (320) described above. Driving assembly (370) includes a pusher member (372) and a push rod assembly (374). Pusher member (372) may be substantially similar to pusher member (322) described above with differences elaborated below; while push rod assembly (374) may be substantially similar to push rod assembly (360) described above, with differences elaborated below.

Push rod assembly (374) includes a translating member (375) and a rotating member (378) having a distal threaded portion (380); which may be substantially similar to translating member (362), rotating member (364), and distal threaded portion (366) described above, with differences elaborated below. Translating member (375) includes an undercut coupling (376) that may help further promote the structural integrity of translating member's (375) coupling with first body (382) of pusher member (372).

Pusher member (372) includes a first body (382) defining threaded opening and having a flange (383), a second body (384) defining threaded opening (386) and having a flange (383); which may be substantially similar to first body (326), threaded openings (330, 338), flange (328), second body (334), and flange (336), described above, with differences elaborated below. In particular, first body (382) and second body (384) together include an expansion feature (390) that allows bodies (382, 384) to expand relative to each other without completely decoupling.

First body (382) includes a projection (392) while second body (384) includes a complementary recess (394). Recess (394) is dimensioned to house projection (392); while projection (392) is dimensioned to vertically actuate within projection (392). Therefore, as shown between FIGS. 21A-21B, if rotating member (364) is rotated to double first body (382) and second body (384), such a decoupling will allow first body (382) and second body (384) to vertically accurate relative to each other, yet projection (393) and recess (394) will help ensure that translation of first body (382) drives translation of second body (384), even when rotating member (364) is decoupled with threaded opening (386). Therefore, when push rod assembly (374) is proximally retracted in order to release tissue (T) in similar fashion to that shown in FIGS. 16D-16E, both first body (382) and second body (384) actuate to the proximal pre-fired position, instead of just first body (326).

In some instances when first body (326) and second body (334) are configured to completely detach, as shown in FIGS. 16D-16E, it may be desirable to have some ability to open and close jaws (150, 152) while flanges (328, 336) actuate relative to each other. Allowing some ability to open and close jaws (150, 152) while first body (326) and second body (334) are decoupled may allow an operator to suitably release tissue (T) without the need of an external manipular to open jaws and close (150, 152).

Figure 22:
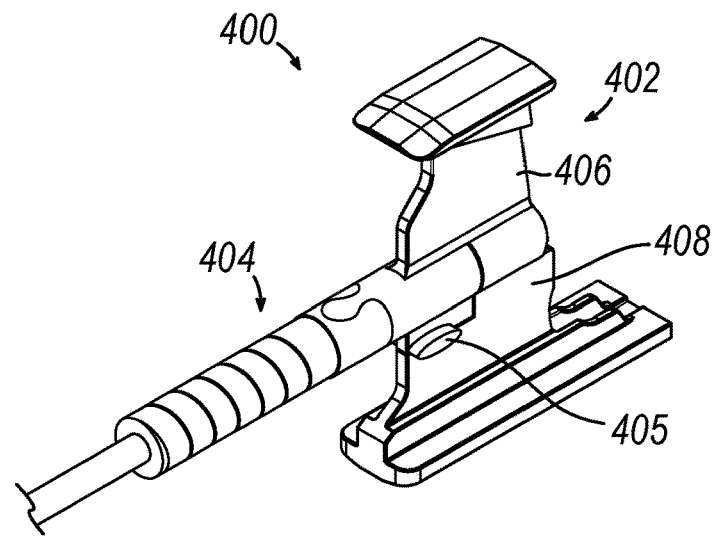
FIG. 22 depicts a perspective view of an alternative driving assembly that may be readily incorporated into the end effector of FIG. 4.
Figure 23:
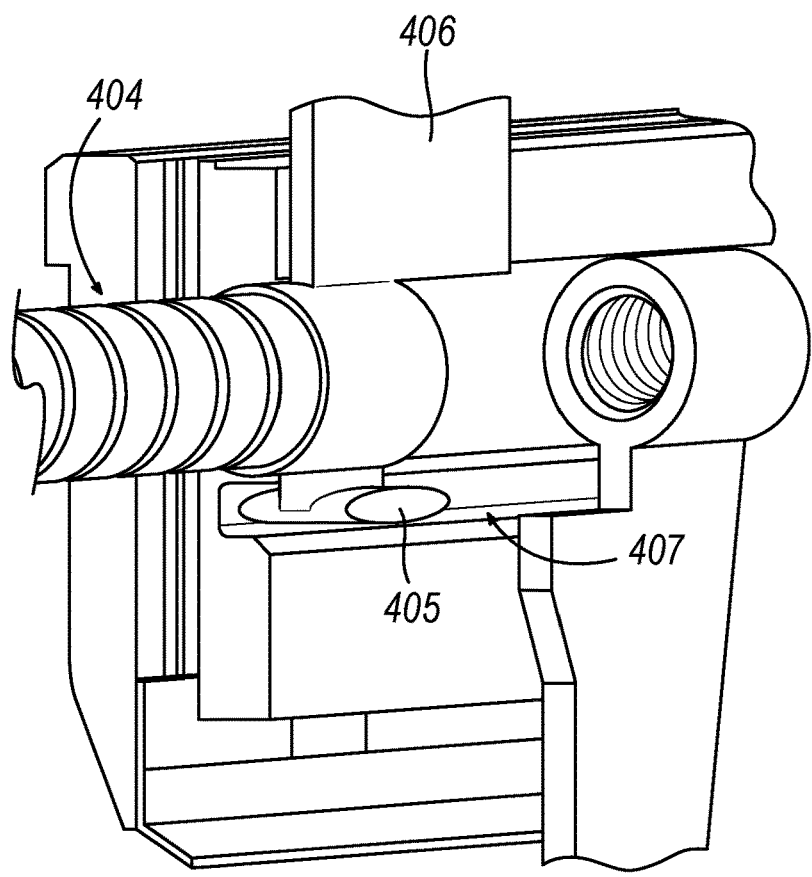
FIG. 23 depicts an enlarged perspective view of a selected portion of the driving assembly of FIG. 22 attached the end effector of FIG. 4.

FIGS. 22-23 show and exemplary driving assembly (400) having a pusher member (402) and a push rod assembly (404). Pusher member (402) may be substantially similar to pusher member (322) described above, with differences elaborated below. Push rod assembly (404) may be substantially similar to push rod assembly (360) described above.

Pusher member (402) includes a first body (406) and a second body (408) that are substantially similar to first body (326) and second body (334) described above, with difference elaborated below. In particular, first body (406) includes a wing (405) dimensioned to slidably fit within a lingual slot (407) defined by removable staple cartridge (154). Wing (405) is configured to suitable interact with slot (407) such that when first body (406) is decoupled from second body (408) in accordance with the description herein, wing (405) and flange of first body (406) may interact with jaws (150, 152) in order to open and close jaws (150, 152) without the need for flange of second body (408) to cam against slot (187) defined by removeable staple cartridge (154). Therefore, in instances where first body (406) is proximally retracted in a similar fashion to that shown in FIGS. 16D-16E, jaw (150) will pivot open due to wing (405) interacting with slot (407) and flange of first body (406) interacting with slot (186). Therefore, in instances where first body (406) is decoupled from second body (408), jaws (150, 152) may still be opened and closed without the need of an external manipulator/force.

III. Exemplary Instrument Having Sequential Firing and Jaw Closure Controlled by One Motor A. Overview of Exemplary Robotic Arm and Instrument As mentioned above, during exemplary use of end effector (210), distal advancement of closure tube (not shown) and closure ring (230) (see FIGS. 10 and 22A-22E) are used to close end effector (210). In other words, distal advancement of closure tube (not shown) and closure ring (230) are used to move lower jaw (212) and anvil jaw (214) toward each other in order to grasp tissue in accordance with the description herein. As also mentioned above, with tissue grasped between staple cartridge (218) and anvil jaw (214), firing beam (216) may then be advanced distally in order to sever and staple tissue in accordance with the description herein. In other words, end effector (210) may be configured such that movement of jaws (212, 214) in order to grasp tissue may be performed independently with respect to actuation of firing beam (216) in order to sever and staple grasped tissue.

Figure 24:
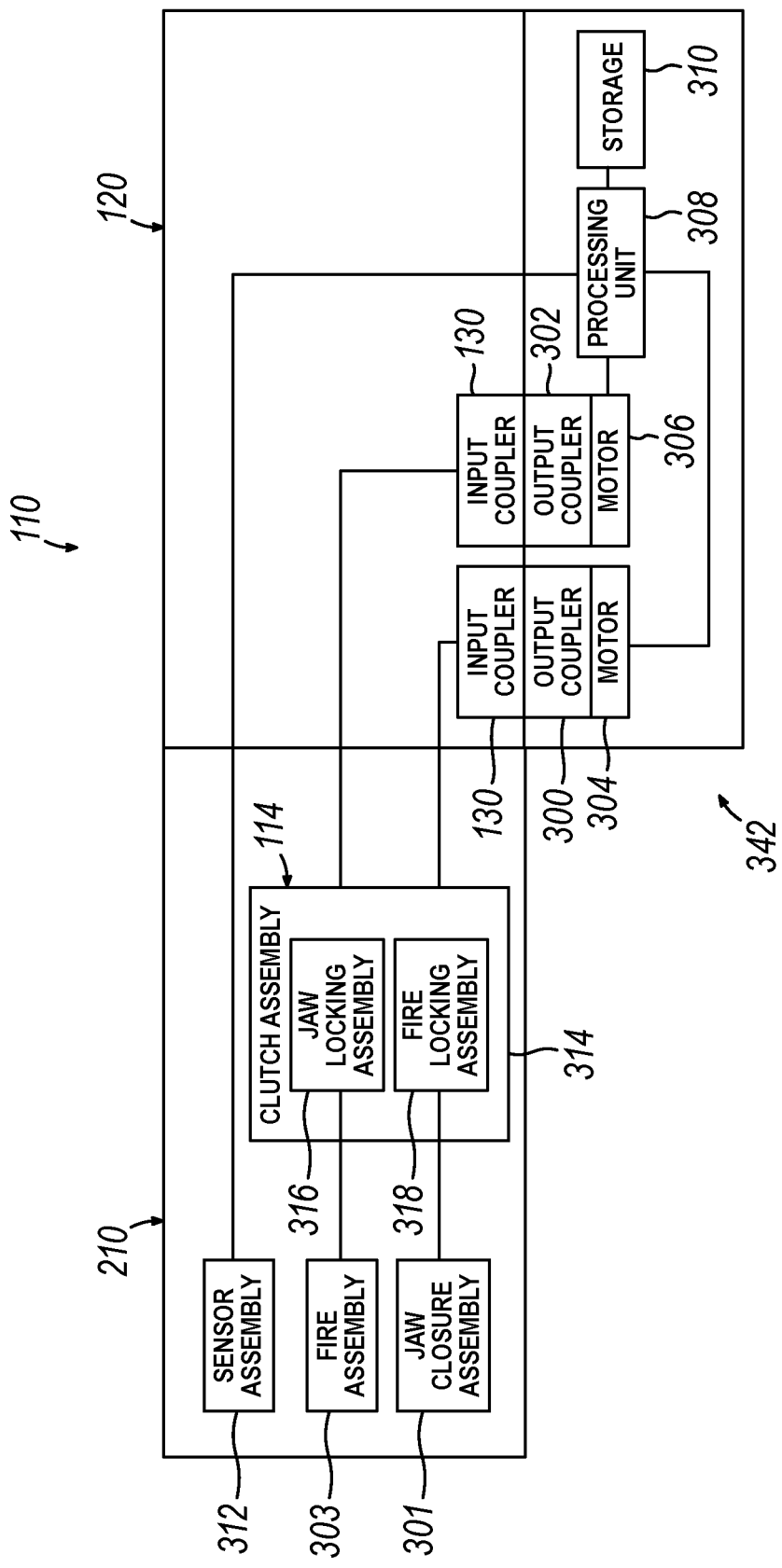
FIG. 24 depicts a schematic view of the instrument of FIG. 4 coupled with the end effector of FIG. 10 and an exemplary robotic arm.

FIG. 24 schematically shows an exemplary robotic arm (342) that may be used to couple with instrument (110) in similar fashion to robotic arm (42) described above. Instrument (110) in the current example (110) incorporated end effector (210) described above, rather than end effector (116). Robotic arm (343) may be substantially similar to robotic arm (42) described above, with differences elaborated below. Therefore, it should be understood that robotic arm (343) may suitably interact with robotic surgical system (10) described above such that a medical professional operator may utilize robotic surgical system (10) to control instrument (110) via robotic arm (343), input control devices (36) of surgeon's console (16), and any other suitable intermediate components as would be apparent to one skilled in the art in view of the teachings herein.

As mentioned above, instrument base (112) includes input couplers (130). Input couplers (130) are configured to interface with and be driven by corresponding output couplers (300, 302) of robotic arm (343). Output couplers (300, 302) may be actuated via one or more robotic motors (304, 306), respectively, which may be controlled by a processing unit (308) in communication with input control devices (36) of surgeon's console (16). Robotic motors (304, 306) may include any suitable components as would be apparent to one skilled in the art in view of the teachings herein. Robotic motors (304, 306) and/or processing unit (308) may include suitable components to measure suitable output characteristics, operating data, etc., of robotic motors (304, 306). For example, robotic motors (304, 306) may include components configured to measure motor temperature, motor displacement, the electrical current used by robotic motors (304, 306), motor power usage (either in a specified unit or represented as a percentage compared to a maximum motor power usage), etc., and may communicate such operating data to processing unit (308) for use of such data in accordance with the description herein.

Processing unit (308) may receive instructions from input control devices (36) in order to actuate robotic motors (304, 306) and corresponding output couplers (300, 302). Processing unit (308) may be in communication with a storage device (310). Processing unit (308) to write data to storage device (310) or access data from storage device (310) in order to operate in accordance with the description herein. While operatively interfacing with input couplers (130), output couplers (300, 302) of robotic arm (343) may be used to actuate selective portions of either end effector (210) or shaft assembly (114) in accordance with the description herein.

End effector (210) includes a jaw closure assembly (301) that includes closure tube (not shown) and closure ring (230), a fire assembly (303) that includes firing beam (216), and a tissue sensor assembly (312). Therefore, jaw closure assembly (301) is configured to open and close jaws (212, 214), while fire assembly (303) is configured to actuate in order to staple and sever tissue grasped by jaws (212, 214) in accordance with the description herein. Both jaw closure assembly (301) and fire assembly (303) are configured to be actuated and controlled independently of each other by a single motor (304).

Sensor assembly (312) is configured to establish communication with processing unit (308) when instrument (110) is operatively coupled with robotic arm (343). Therefore, data obtained from sensor assembly (312) may be stored on storage device (310) for later access by processing unit (308). Sensor assembly (312) may include one or more sensors configured to measure any suitable data as would be apparent to one skilled in the art in view of the teachings herein. For instance, sensor assembly (312) may be configured to measure a tissue load imparted on the jaws (212, 214) while grasping tissue in accordance with the description herein. Additionally, or alternatively, sensor assembly (312) may be configured to measure the locations tissue is in contact with jaws (212, 214) while grasping tissue in accordance with the description herein.

Shaft assembly (114) in the current example includes a clutch assembly (314) configured to alternate between which assembly (301, 303) motor (304) is configured to actuate. Clutch assembly (314) alternate between which assembly (301, 303) motor (304) may drive via a second motor (306), or any other suitable structures as would be apparent to one skilled in the art in view of the teachings herein.

Additionally, clutch assembly (314) includes locking assemblies (316, 318) configured to maintain the position of the assembly (301, 303) not operatively engaged with motor (304) without utilizing any motor power from motor (304). In other words, when fire assemble (303) is not operatively engaged with motor (304), fire locking assembly, also referred to as clutch assembly (314) may ensure the position of firing beam (216) remains fixed relative to shaft assembly (114). Conversely, when jaw closure assembly (301) is not operatively engaged with motor (304), jaw locking assembly (316) may ensure the position of closure ring (230) remains fixed relative to shaft assembly (114). Therefore, when motor (304) is configured to actuate jaw closure assembly (301), fire locking assembly (318) may be activated to prevent unwanted movement of firing beam (216) without utilizing any power from motor (304); and when motor (3040 is configured to actuate fire assembly (303), jaw locking assembly 9316) may be activated to prevent unwanted movement of closure ring (230) without utilizing any power from motor (304). It should be understood that clutch assembly (314), jaw locking assembly (316), and fire locking assembly (318) may have any suitable components as would be apparent to one skilled in the art in view of the teachings herein.

B. Exemplary Algorithm for Sequentially Closing Jaws and Actuating Firing Assembly to Actively Reduce Required Firing Force While end effector (210) is used to staple and sever grasped tissue, distal advancement of firing beam (216) (see FIG. 11) may be inhibited such that robotic surgical system (10) may have to power robotic motor (304) past a predetermined maximum power output level in order to distally advance firing beam (216) further. In some instances, rather than using robot motor(s) past a predetermined power output level to further staple and sever grasped tissue is accordance with the description herein, robotic motor (304) may be programed to temporarily stop, stall, halt, or otherwise delay advancement of firing beam (216) for a predetermined amount of time once the predetermined maximum motor power output level for advancing firing beam (216) is reached. In such instances, the temporary delay of advancing firing beam (216) may act as a passive means of reducing the required firing force for robotic motor (304) to distally advance firing beam (216). This passive means of reducing the required firing force may allow for a "milking effect" to occur between jaws (212, 214) and grasped tissue (e.g., where tissue is effectively squeezed out from the space between jaws (212, 214)), thereby reducing the amount of force required for firing beam (216) to staple and sever tissue in accordance with the teachings herein.

In some instances, instead of passively waiting for the "milking effect" to reduce the force required for robotic motor (304) to distally advance firing beam (216) without exceeding a predetermined power output level of robotic motor (304), it may be desirable to actively reduce the firing force required for robotic motor (304) to advance firing beam (216) to thereby prevent robotic motor (304) from operating past the predetermined power output level.

Figure 25:
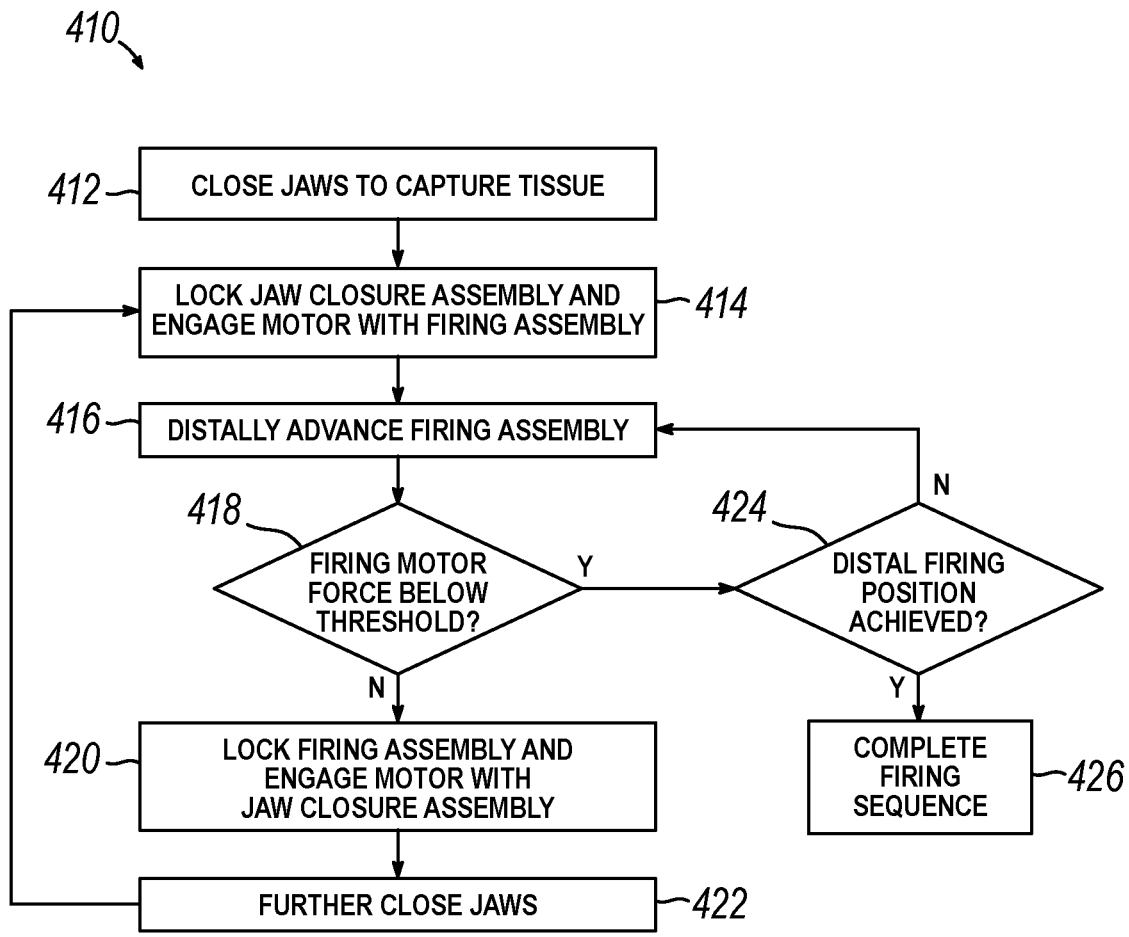
FIG. 25 depicts a block diagram of an exemplary motor control algorithm that may be used by the robotic arm of FIG. 24.
Figure 27:
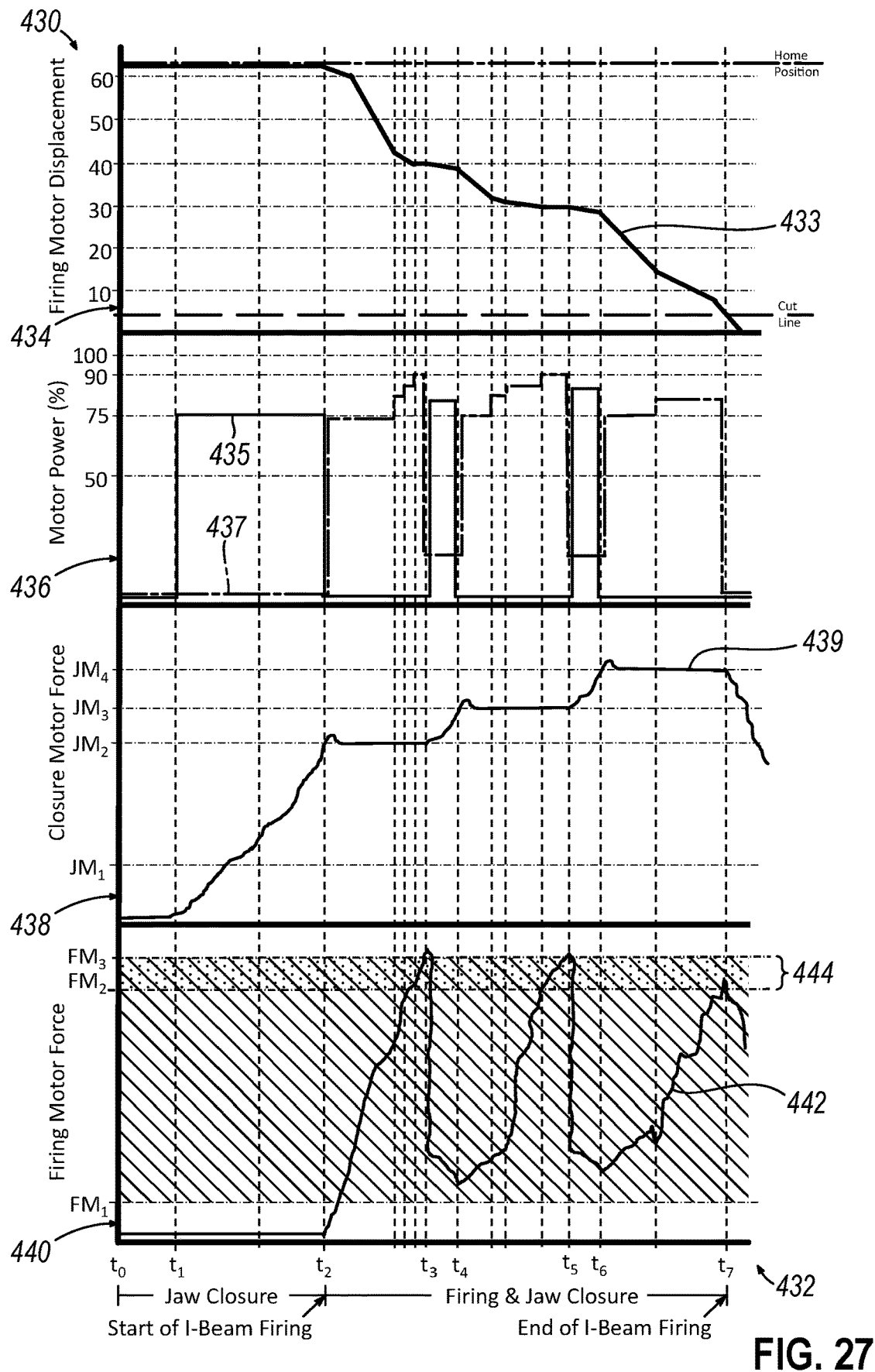
FIG. 27 depicts a graph representing the firing displacements, mort power, jaw closure force, and firing force over time of the firing sequence shown in the table of FIG. 26.

FIG. 25 shows a motor control algorithm (410) that may be utilized by robotic surgical instrument (110), end effector (210), and robotic arm (343) described above. FIG. 26 shows an exemplary use of motor control algorithm (410) at various times (t0, t1, t2, t3, t4, t5, t6, t7) during the firing process; while FIG. 27 shows a graph (430) representing the firing displacement (434) caused when motor (304) is operatively coupled to fire assembly (303), the motor power output (436) transmitted to both jaw closure assembly (301) and fire assembly (303) represented as a percentage, the closure force (438) on jaw closure assembly (301), and the firing force (440) on fire assembly (303), all measured over the time (432) elapsed during exemplary use of the algorithm as shown in FIG. 26.

First, as shown between times (t0), (t1), and (t2), an operator may utilize input control devices (36) of surgeon's console (16) to manipulate end effector (210) in grasping tissue (T) of a patient. This may be represented as block (422) in motor control algorithm (410) shown in FIG. 25. The initial closure of jaws (212, 214) to grasp tissue (T) is represented on graph (430) of FIG. 27 between time (t0) and time (t2).

It should be understood that motor (304) is operatively engaged with jaw closure assembly (301) such that fire locking assembly (318) of clutch assembly (314) may be activated to substantially lock the position of firing beam (216) relative to shaft assembly (114). Therefore, since actuation of firing beam (216) has not yet happened, firing displacement line (433) (which represents the longitudinal position of pusher block (236)), firing power line (437) (which represents output power of motor (304) with regards to fire assembly (303)), and firing force line (442) (which represents the force generated in order to drive firing beam (216)) remain relative unchanged between times (t0) and (t2).

However, with motor (304) operative engaged with jaw closure assembly (301) to drive closure ring (230) distally to close jaws (212, 214), the jaw closure power line (435) (which may represent output power of motor (304) with regards to jaw closure assembly (301) raises from little or no power output up to 75% in the current example in order to manipulate jaws (212, 214) to grasp tissue (T). Additionally, the closure force line (439) (which represents the force imparted on jaw closure assembly (301) in order to grasp tissue (T)) increases to JM2 in response to motor (304) driving jaws (212, 214) to grasp tissue (T). Therefore, between times (t0) and (t2), motor (304) is activated to drive jaws (212, 214) such that the reactive closure force line (439) gradually increases due to contact between grasped tissue (T) and jaws (212, 214).

When the operator is ready to sever and staple tissue (T) grasped between jaws (212, 214), the operator may initiate the firing sequence via surgeon's console (16). In response, as shown in block (414) of motor control algorithm (410), motor (306) may drive clutch assembly (314) such that motor (304) is operatively engaged with fire assembly (303), rather than jaw closure assembly (301). It should be understood that when motor (304) is operatively engaged with fire assembly (303), jaw locking assembly (316) of clutch assembly (314) may be activated to substantially lock the position of closure ring (230) relative to shaft assembly (114). Therefore, as shown between times (t2) and (t3), the jaw closure power line (435) may drop to substantially zero while closure force line (439) remains at around the same level between times (t2) and (t3), since motor (304) is not needed to maintain the closed position of jaws (212, 214) between times (t2) and (t3).

With motor (304) operatively engaged with fire assembly (303), motor (304) may advance firing beam (216) distally, as shown in block (416) of motor control algorithm (410) and as shown between times (t2) and (t3). Advancement of firing beam (216) changes the firing displacement line (433), increases firing power line (437), and increases firing force line (442). Motor control algorithm may ask if the firing force line (442) imparted on motor (304) is below a predetermined threshold, as shown in block (418). If firing force line (442) never raises above the predetermined threshold, motor (304) will continue to advance firing beam (216) until distal firing position is achieved, as shown in block (424). Once the distal firing position is achieved, motor (304) may retract firing beam (216) in order to complete the firing stroke (426).

However, if it is determined that the firing force (442) reaches a predetermined range (444), as shown in FIG. 27, motor control algorithm (410) may instruct motor (304) to stop the distal advancement of firing beam (216), lock fire assembly (303), and engage motor (304) with jaw closure assembly (301) in accordance with the description herein, and as shown in block (420) of the motor control algorithm (410). With motor (304) engaged with jaw closure assembly (301), motor (304) may further close jaws (212, 214) as shown in block (422) of the motor control algorithm (410).

Further closure of jaws (212, 214) thereby increases both jaw closure power line (435) and closure force line (439) between times (t3) and (t4). Further closure of jaws (212, 214) may actively decrease the amount of firing force required for motor (304) to distally advance firing beam (216). It should be understood that since fire locking assembly, also referred to as clutch assembly (314) is activated, the position of firing beam (216) may not substantially change during times (t3) and (t4).

Once jaws (212, 214) are sufficiently closed further, motor (304) may switch back to being operatively engaged with fire assembly (303) in accordance with the description herein. Motor (304) may then begin to advance fire beam (216) in accordance with the description herein. If the firing force line (442) increase back into the undesirable predetermined range (444), motor (304) may actively engage jaw closure assembly (301) once again in order to further close jaws (212, 214), as shown between times (t5) and (t6), in order to actively reduce the firing force required to advance firing beam (216).

Therefore, it should be understood the motor control algorithm (410) may allow a single motor (304) to control both a jaw closure assembly (301) and a fire assembly (303), and cycle between operative engagement with both assemblies (301, 303) in a cooperative fashion in order to actively reduce the firing force required, which may (A) reduce the time required to complete a the firing process of firing beam (216) in accordance with the description herein, and (B) reduce the chances of having to operate motor (304) past a predetermined threshold or operate manual actuator (124).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) an end effector, the end effector including: (i) a first jaw, (ii) a second jaw, (iii) a blade, (iv) a plurality of staples, (v) a jaw closure assembly operable to pivot the first jaw toward the second haw, and (vi) a firing assembly including a firing member, the firing member being operable to one or both of drive the blade through tissue or drive the plurality of staples into tissue; and (b) a drive system configured to: (i) drive the jaw closure assembly to thereby pivot the first jaw toward the second jaw to a first closed position, (ii) operatively disengage the jaw closure assembly and operatively engage the firing assembly, (iii) distally advance the firing member of the firing assembly to one or both of drive the blade through tissue or drive the plurality of staples into tissue, (iv) detect an initiation condition, (v) in response to detecting the initiation condition, operatively disengage the firing assembly and operatively re-engage the jaw closure assembly, (vi) drive the jaw closure assembly to further pivot the first jaw toward the second jaw to a second closed position, (vii) operatively disengage the jaw closure assembly and operatively re-engage the firing assembly, and (viii) distally advance the firing member further within the end effector to one or both of further drive the blade through tissue or further drive the plurality of staples into tissue.

Example 2

The apparatus of Example 1, wherein the drive system is further configured to activate a jaw locking assembly to maintain the first jaw and the second jaw in the first closed position.

Example 3

The apparatus of Example 2, wherein the drive system is further configured to activate the jaw locking assembly to maintain the first jaw and the second jaw in the first closed position after operatively disengaging the jaw closure assembly.

Example 4

The apparatus of any of Examples 1 through 3, wherein the drive system is further configured to activate a fire locking assembly to maintain a longitudinal position of the firing member.

Example 5

The apparatus of any of Examples 1 through 4, the drive system including a motor operable to distally advance the firing member, wherein the drive system is further configured to detect the initiation condition by detecting a predetermined power level used by the motor to distally advance the firing member.

Example 6

The apparatus of any of Examples 1 through 5, wherein the end effector comprises a replaceable staple cartridge containing the plurality of staples.

Example 7

The apparatus of Example 6, wherein the replaceable staple cartridge further comprises the blade.

Example 8

The apparatus of any of Examples 1 through 7, the drive system further comprising a first motor and a clutch assembly, the clutch assembly being configured to transition the first motor between operative engagement with the jaw closure assembly and the firing assembly.

Example 9

The apparatus of Example 8, the drive system further comprising a second motor, wherein the second motor is operable to drive the clutch assembly.

Example 10

The apparatus of Example 9, further comprising a robotic arm, wherein the first motor and the second motor are contained within the robotic arm.

Example 11

The apparatus of Example 10, wherein the robotic arm further comprises a processing unit in communication with a surgeon's console.

Example 12

The apparatus of Example 11, wherein the robotic arm comprises a storage device.

Example 13

The apparatus of any of Examples 1 through 12, wherein the end effector further comprises a sensor assembly.

Example 14

The apparatus of Example 13, wherein the sensor assembly is configured detect to the initiation condition.

Example 15

The apparatus of any of Examples 1 through 14, wherein the initiation condition comprises a measured operating condition of a motor of the drive system or a measured force acting on the firing member

Example 16

An apparatus, comprising: (a) a shaft assembly; (b) an actuating member configured to actuate within the shaft assembly; and (c) an end effector extending distally from the shaft assembly, wherein the end effector comprises: (i) a first jaw defining a first longitudinal slot, (ii) a second jaw defining a second longitudinal slot, wherein the first jaw and the second jaw are configured to actuate relative to each other between an open position and a closed position, and (iii) a pusher member attached to a distal end of the actuating member, wherein the pusher member comprises: (A) a first flange slidably housed within the first longitudinal slot, wherein the first flange comprises a first tapered proximal surface configured to cam against the first longitudinal slot in order to actuate the first jaw toward the open position, and (B) a second flange slidably housed within the second longitudinal slot, wherein the second flange comprises a second tapered proximal surface configured to cam against the second longitudinal slot in order to actuate the second jaw toward the open position.

Example 17

The apparatus of Example 16, wherein the first flange comprises a first tapered distal surface configured to cam against the first longitudinal slot in order to actuate the first jaw toward the closed position.

Example 18

The apparatus of any of Examples 16 through 17, wherein the second flange comprises a second tapered distal surface configured to cam against the second longitudinal slot in order to actuate the second jaw toward the closed position.

Example 19

The apparatus of any of Examples 16 through 18, wherein the second jaw further comprises a removeable staple cartridge.

Example 20

An apparatus, comprising: (a) a shaft assembly; (b) an actuating member configured to actuate within the shaft assembly; and (c) an end effector extending distally from the shaft assembly, wherein the end effector comprises: (i) a first jaw defining a first longitudinal slot, (ii) a second jaw defining a second longitudinal slot, wherein the first jaw and the second jaw are configured to actuate relative to each other between an open position and a closed position, and (iii) a pusher member attached to a distal end of the actuating member, wherein the pusher member comprises: (A) a first flange slidably housed within the first longitudinal slot, and (B) a second flange slidably housed within the second longitudinal slot, and (C) a coupling member configured to selectively couple and decouple the first flange from the second flange in order to allow the first flange to vertically move relative to the second flange to thereby allow the first jaw and the second jaw to acuate toward the open position.

V. Miscellaneous

Any one or more of the teachings, expressions, embodiments, examples, etc.

described herein may be combined with any one or more of the teachings, expressions, embodiments, examples, etc. described in U.S. patent application Ser. No. 17/402,674, entitled "Methods of Operating a Robotic Surgical Stapler," filed on Aug. 16, 2021, published as U.S. Pub. No. 2023/0051361 on Feb. 16, 2023; U.S. patent application Ser. No. 17/402,675, entitled "Multi-Threshold Motor Control Algorithm for Powered Surgical Stapler," filed on Aug. 16, 2021, published as U.S. Pub. No. 2023/0051271 on Feb. 16, 2023; U.S. patent application Ser. No. 17/402,677, entitled "Variable Response Motor Control Algorithm for Powered Surgical Stapler," filed on Aug. 16, 2021, published as U.S. Pub. No. 2023/0048444 on Feb. 16, 2023; U.S. patent application Ser. No. 17/402,695, entitled "Firing System Features for Surgical Stapler," filed on Aug. 16, 2021, published as U.S. Pub. No. 2023/0050707 on Feb. 16, 2023; U.S. patent application Ser. No. 17/402,701, entitled "Multiple-Sensor Firing Lockout Mechanism for Powered Surgical Stapler," filed on Aug. 16, 2021, published as U.S. Pub. No. 2023/0050358 on Feb. 16, 2023; U.S. patent application Ser. No. 17/402,703, entitled "Proximally Located Firing Lockout Mechanism for Surgical Stapler," filed on Aug. 16, 2021, published as U.S. Pub. No. 2023/0051105 on Feb. 16, 2023; U.S. patent application Ser. No. 17/402,720, entitled "Cartridge-Based Firing Lockout Mechanism for Surgical Stapler," filed on Aug. 16, 2021, published as U.S. Pub. No. 2023/0051222 on Feb. 16, 2023; U.S. patent application Ser. No. 17/402,732, entitled "Sled Restraining Member for Surgical Stapler," filed on Aug. 16, 2021, published as U.S. Pub. No. 2023/0045893 on Feb. 16, 2023; U.S. patent application Ser. No. 17/402,738entitled "Firing Member Tracking Feature for Surgical Stapler," filed on Aug. 16, 2021, published as U.S. Pub. No. 2023/0049736 on Feb.16, 2023; U.S. patent application Ser. No. 17/402,744, entitled "Adjustable Power Transmission Mechanism for Powered Surgical Stapler," filed on Aug. 16, 2021, published as U.S. Pub. No. 2023/0051938 on Feb. 16, 2023; U.S. patent application Ser. No. 17/402,749, entitled "Firing Bailout System for Powered Surgical Stapler," filed on Aug. 16, 2021, published as U.S. Pub. No. 2023/0045998 on Feb. 16, 2023; and/or U.S. patent application Ser. No. 17/402,759, entitled "Deflectable Firing Member for Surgical Stapler," filed on Aug. 16, 2021, published as U.S. Pub. No. 2023/0052307 on Feb. 16, 2023. The disclosure of each of these applications is incorporated by reference herein in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
(a) an end effector, the end effector including:
  (i) a first jaw,
  (ii) a second jaw,
  (iii) a blade,
  (iv) a plurality of staples,
  (v) a jaw closure assembly operable to pivot the first jaw toward the second haw, and
  (vi) a firing assembly including a firing member, the firing member being operable to one or both of drive the blade through tissue or drive the plurality of staples into tissue; and
(b) a drive system configured to:
  (i) drive the jaw closure assembly to thereby pivot the first jaw toward the second jaw to a first closed position,
  (ii) operatively disengage the jaw closure assembly and operatively engage the firing assembly,
  (iii) distally advance the firing member of the firing assembly to one or both of drive the blade through tissue or drive the plurality of staples into tissue,
  (iv) detect an initiation condition,
  (v) in response to detecting the initiation condition, operatively disengage the firing assembly and operatively re-engage the jaw closure assembly,
  (vi) drive the jaw closure assembly to further pivot the first jaw toward the second jaw to a second closed position,
  (vii) operatively disengage the jaw closure assembly and operatively re-engage the firing assembly, and
  (viii) distally advance the firing member further within the end effector to one or both of further drive the blade through tissue or further drive the plurality of staples into tissue.

2. The apparatus of claim 1, wherein the drive system is further configured to activate a jaw locking assembly to maintain the first jaw and the second jaw in the first closed position.

3. The apparatus of claim 2, wherein the drive system is further configured to activate the jaw locking assembly to maintain the first jaw and the second jaw in the first closed position after operatively disengaging the jaw closure assembly.

4. The apparatus of claim 1, wherein the drive system is further configured to activate a fire locking assembly to maintain a longitudinal position of the firing member.

5. The apparatus of claim 1, the drive system including a motor operable to distally advance the firing member, wherein the drive system is further configured to detect the initiation condition by detecting a predetermined power level used by the motor to distally advance the firing member.

6. The apparatus of claim 1, wherein the end effector comprises a replaceable staple cartridge containing the plurality of staples.

7. The apparatus of claim 6, wherein the replaceable staple cartridge further comprises the blade.

8. The apparatus of claim 1, the drive system further comprising a first motor and a clutch assembly, the clutch assembly being configured to transition the first motor between operative engagement with the jaw closure assembly and the firing assembly.

9. The apparatus of claim 8, the drive system further comprising a second motor, wherein the second motor is operable to drive the clutch assembly.

10. The apparatus of claim 9, further comprising a robotic arm, wherein the first motor and the second motor are contained within the robotic arm.

11. The apparatus of claim 10, wherein the robotic arm further comprises a processing unit in communication with a surgeon's console.

12. The apparatus of claim 11, wherein the robotic arm comprises a storage device.

13. The apparatus of claim 1, wherein the end effector further comprises a sensor assembly.

14. The apparatus of claim 13, wherein the sensor assembly is configured detect to the initiation condition.

15. The apparatus of claim 1, wherein the initiation condition comprises a measured operating condition of a motor of the drive system or a measured force acting on the firing member.

* * * * *